(12) United States Patent
Noda et al.

(10) Patent No.: US 9,018,438 B2
(45) Date of Patent: Apr. 28, 2015

(54) SCREENING METHOD FOR ANTICANCER DRUGS

(75) Inventors: Makoto Noda, Kyoto (JP); Ryuya Murai, Kyoto (JP); Hitoshi Kitayama, Kyoto (JP); Yoko Yoshida, Kyoto (JP)

(73) Assignee: Kyoto University, Kyoto (JP)

( * ) Notice: Subject to any disclaimer, the term of this patent is extended or adjusted under 35 U.S.C. 154(b) by 0 days.

(21) Appl. No.: 13/812,715

(22) PCT Filed: Jul. 29, 2011

(86) PCT No.: PCT/JP2011/067393
§ 371 (c)(1),
(2), (4) Date: Mar. 11, 2013

(87) PCT Pub. No.: WO2012/015023
PCT Pub. Date: Feb. 2, 2012

(65) Prior Publication Data
US 2013/0167255 A1    Jun. 27, 2013

Related U.S. Application Data

(60) Provisional application No. 61/368,807, filed on Jul. 29, 2010.

(51) Int. Cl.
*A01K 67/00*   (2006.01)
*G01N 33/50*   (2006.01)

(52) U.S. Cl.
CPC .... *G01N 33/5011* (2013.01); *A01K 2267/0331* (2013.01)

(58) Field of Classification Search
None
See application file for complete search history.

(56) References Cited

U.S. PATENT DOCUMENTS 4,161,526 A * 7/1979 Gorman .......................... 514/188
4,699,912 A * 10/1987 Dickneite et al. ............. 514/283
5,650,135 A     7/1997 Contag et al.

FOREIGN PATENT DOCUMENTS

| JP | 9-234082 | 9/1997 |
| JP | 2000-502884 | 3/2000 |
| JP | 2008-237098 | 10/2008 |
| WO | 97/18841 | 5/1997 |
| WO | 97/24439 | 7/1997 |

OTHER PUBLICATIONS

Malcolm et al., Expert Opin. Drug Saf., 2008, 7: 459-472.*
Takahashi et al., Proc. Natl. Acad. Sci. USA, 1998, 95: 13221-13226.*
Makridou et al., Genesis, 2003, 36: 83-87.*
Ohta et al., British Journal of Cancer, 1997, 75: 512-515.*
Kelkar et al., Biochim. Biophys. Acta, 2007, 1768: 2011-2025.*
Ivanov et al., Tsiitologia, 2004, 46: 740-747; Abstract.*
Yamagaki et al., J. Am. Soc. Mass Spectrom., 2007, 18: 714-723.*
English translation of the International Preliminary Report on Patentability dated Feb. 21, 2013.
International Search Report issued Oct. 11, 2011 in International (PCT) Application No. PCT/JP2011/067393.
English translation of the Reply to Written Opinion, Nov. 10, 2011.
N. Yamamoto et al., "Real-Time GFP Imaging of Spontaneous HT-1080 Fibrosarcoma Lung Metastases", Clinical & Experimental Metastasis, vol. 20, No. 2, pp. 181-185, 2003.
I. Osawa et al., "Luciferase o Riyo Shita Gan Kenkyu", Biophilia, vol. 1, No. 2, pp. 33-37, 2005 with partial English translation.
M. Hashida et al., "Suppression of Cancer Metastasis by Cell-Specific Gene Transfer Therapy Targeted for Oxygen Radical Elimination Enzyme", Ministry of Education, Culture, Sports, Science and Technology Tokutei Ryoiki Kenkyu "Gan" Kenyu Hokoku Shuroku Heisei 15 Nendo <2003 Nendo>, pp. 307-309, Jan. 28, 2005 with partial English translation.
I. Osawa et al., "Rat o Mochita Morateki Kogan'yaku Screening-kei no Kakuritsu-1. Bio Translation is Imaging System", Japanese Journal of Clinical attached Pharmacology, vol. 36, Suppl. p. S172, 2P-033, Nov. 15, 2005 with partial English translation.
S. H. Thorne et al., "Using In Vivo Bioluminescence Imaging to Shed Light on Cancer Biology", Proceeding of the IEEE, vol. 93, No. 4, pp. 750-762, Apr. 2005.
M. Noda et al., "Recklessness as a Hallmark of Aggressive Cancer", Cancer Science, vol. 98, No. 11, pp. 1659-1665, Nov. 2007.
R. M. Sasahara et al., "Involvement of the Sp1 Site in ras-Mediated Downregulation of the RECK Metastasis Suppressor Gene", Biochemical and Biophysical Research Communications, vol. 264, No. 3, pp. 668-675, 1999.
R. Murai et al., "A Novel Screen Using the Reck Tumor Suppressor Gene Promoter Detects both Conventional and Metastasis-Suppressing Anticancer Drugs", Oncotarget, vol. 1, No. 4, pp. 252-264, 2010.
R. Murai et al., "A Novel Screen for Anticancer Drugs Using the Cells Harboring Reck-Promoter-Reporter and Inducible HRAS12V Oncogene", Dai 69 Kai Proceedings of the Japanese Cancer Association, pp. 271-272, 0-412, Aug. 2010.
J. Oh et al., "The Membrane-Anchored MMP Inhibitor Reck is a Key regulator of Extracellular Matrix Integrity and Angiogenesis", Cell, vol. 107, pp. 789-800, Dec. 14, 2001.
M. Noda et al., "RECK: A Novel Suppressor of Malignancy Linking Oncogenic Signaling to Extracellular Matrix Remodeling", Cancer and Metastasis Reviews, vol. 22, pp. 167-175, 2003.

(Continued)

*Primary Examiner* — Ileana Popa
(74) *Attorney, Agent, or Firm* — Wenderoth, Lind & Ponack, L.L.P.

(57) ABSTRACT

Use of an animal model of spontaneous metastasis bearing a tumor derived from a cell line RM72 (Accession No. NITE BP-1110) allows simultaneous evaluation of tumorigenesis and spontaneous cancer metastasis. Use of a screening method using the animal model of spontaneous metastasis allows the obtainment of a substance having an anticancer activity and/or an anti-metastatic activity. Use of another screening method for selecting a substance that increases the expression of RECK in a cancer cell allows the obtainment of a substance that can serve as an active ingredient in an anticancer drug.

9 Claims, 14 Drawing Sheets

(56) References Cited

OTHER PUBLICATIONS

M. Noda et al., "Recklessness as a Hallmark of Aggressive Cancer", Cancer Sci., vol. 98, No. 11, pp. 1659-1665, Nov. 2007.

I. J. Fidler et al., "Selection of Successive Tumour Lines for Metastasis", Nature New Biology, vol. 242, pp. 148-149, 1973.

I. J. Fidler et al., "The Relationship of Embolic Homogeneity, Number, Size and Viability to the Incidence of Experimental Metastasis", Eur. J. Cancer, vol. 9, pp. 223-227, 1973.

C. J. Fitzer-Attas et al., "Modification of PDGFα Receptor Expression or Function Alters the Metastatic Phenotype of 3LL Cells", Oncogene, vol. 15, pp. 1545-1554, 1997.

* cited by examiner

SCREENING METHOD FOR ANTICANCER DRUGS

This application is a U.S. national stage of International Application No. PCT/JP2011/067393 filed Jul. 29, 2011, which claims the benefit of U.S. provisional application Ser. No. 61/368,807 filed Jul. 29, 2010.

TECHNICAL FIELD

The present invention relates to a screening method for an anticancer drug. In particular, the present invention relates to a screening method for an anticancer drug using an animal model of spontaneous cancer metastasis; an animal model of spontaneous cancer metastasis to be used in the screening method; a cancer cell line to be used in the production of the animal model; a screening method for an anticancer drug, the method comprising selecting a substance that increases the expression of RECK in a cancer cell; a mammalian cell to be used in the screening method; and an anticancer drug comprising as an active ingredient a compound selected by the screening method.

BACKGROUND ART

Classical screening methods for anticancer drugs have been based on their activities to kill cancer cells or to induce shrinkage of tumor grafts. The drugs selected by these methods, however, generally have serious side effects and narrow ranges of tolerated doses. Recently molecular-targeted drugs have been spotlighted, but in most cases they are applicable only to tumors bearing genetic alterations in a specific gene and a second mutation could develop resistant cells. Therefore there is a pressing need to discover drugs with few side effects and strong anticancer activities.

The inventors have established an original screening system for malignant transformation suppressor genes and using this system found out novel cancer-associated genes. It has been revealed that, among the novel cancer-associated genes that the inventors have found out, the RECK (reversion-inducing-cysteine-rich protein with kazal motifs) gene encoding a membrane-anchored metalloproteinase-regulator is often down-regulated in various types of cancers such as large intestine, lung, stomach, breast, pancreas, and prostate cancers and the expression of the RECK gene in tumor tissues positively correlates with the survival of the patients. In addition, transplantation of a cancer cell line with forced expression of the RECK gene into nude mice resulted in more suppression of tumor proliferation, angiogenesis, invasion, metastasis, and the like as compared to transplantation of the parent strain. These findings imply that RECK is not only a useful prognosis marker but also a promising target molecule to be activated (effector) in cancer therapy (Non Patent Literature 1, 2 and 3).

In cancer metastasis experiments, the most commonly used assay is a method in which two to eight weeks after injection of melanoma cells into the tail veins of mice, the mice are dissected and the number of the colonies developed in the lungs is counted (tail vein assay) (Non Patent Literature 4 and 5). This assay is also referred to as "experimental metastasis assay" and considered to be the reproduction of the later stage of hematogenous metastasis. Another method in which injection of tumor cells into a particular tissue results in the development of tumors at distant tissues is more close to metastasis in actual patients and is referred to as "spontaneous metastasis assay". One of known spontaneous metastasis protocols is that tumors are inoculated into the foot-pad of mice; once the tumors reach a predetermined size, the tumor-bearing foot is amputated for removal of the primary tumors; and 40 to 100 days later the mice are dissected for examination of lung metastasis (Non Patent Literature 6). These assays, however, require a long time for the results to show up and therefore there is a need to establish an experimental system to evaluate spontaneous metastasis in a short period of time.

CITATION LIST

Non Patent Literature

Non Patent Literature 1: Oh J, Takahashi R, Kondo S, Mizoguchi A, Adachi E, Sasahara R M, Nishimura S, Imamura Y, Kitayama H, Alexander D B, Ide C, Horan T P, Arakawa T, Yoshida H, Nishikawa S, Itoh Y, Seiki M, Itohara S, Takahashi C, Noda M. The membrane-anchored MMP inhibitor RECK is a key regulator of extracellular matrix integrity and angiogenesis. Cell 107, 789-800 (2001).
Non Patent Literature 2: Noda M, Oh J, Takahashi R, Kondo S, Kitayama H, Takahashi C. RECK: a novel suppressor of malignancy linking oncogenic signaling to extracellular matrix remodeling. Cancer Metastasis Rev 22, 167-175 (2003).
Non Patent Literature 3: Noda M, Takahashi C. Recklessness as a hallmark of aggressive cancer. Cancer Sci 98, 1659-1665 (2007).
Non Patent Literature 4: Fidler I J. Selection of successive tumour lines for metastasis. Nat New Biol 242, 148-149 (1973).
Non Patent Literature 5: Fidler I J. The relationship of embolic homogeneity, number, size and viability to the incidence of experimental metastasis. Eur J Cancer 9, 223-227 (1973).
Non Patent Literature 6: Fitzer-Attas C J, Do M S, Feigelson S, Vadai E, Feldman M, Eisenbach L. Modification of PDGFalpha receptor expression or function alters the metastatic phenotype of 3LL cells. Oncogene 15, 1545-1554 (1997).

SUMMARY OF INVENTION

Technical Problem

An object of the present invention is to provide a cancer cell line to be used in a short-term evaluation of spontaneous metastasis, an animal model of spontaneous cancer metastasis using the cancer cell line, a method for producing the animal model, a screening method using the animal model of spontaneous cancer metastasis, and an anticancer drug or cancer metastasis suppressor obtained by the screening method. Another object of the present invention is to provide a screening method for selecting a substance that increases the expression of RECK in a cancer cell, a mammalian cell to be used in the screening method, and an anticancer drug obtained by the screening method.

Solution to Problem

The present invention to solve the above problems includes the following aspects.
[1] An RM72 cell (Accession No. NITE BP-1110).
[2] An animal model of spontaneous cancer metastasis bearing a tumor derived from the cell according to the above [1].

[3] The animal model of spontaneous cancer metastasis according to the above [2], wherein the animal is a rodent.

[4] The animal model of spontaneous cancer metastasis according to the above [3], wherein the animal is a mouse.

[5] A method for producing an animal model of spontaneous cancer metastasis, the method comprising inoculating the cell according to the above [1] into an experimental animal.

[6] The method for producing an animal model of spontaneous cancer metastasis according to the above [5], wherein the method comprises subcutaneously inoculating the cell according to the above [1] into an experimental animal to develop a tumor.

[7] A screening method for a substance having an anticancer activity and/or a cancer metastasis suppressing activity, the method comprising the steps of
administering a test substance to the animal model of spontaneous cancer metastasis according to any of the above [2] to [4],
determining the tumor size in the cell-inoculation site and the metastatic focus number and/or the metastatic focus size in a target organ after the start of the administration of the test substance, and
comparing the tumor size in the cell-inoculation site and the metastatic focus number and/or the metastatic focus size in a target organ between the animal with the administration of the test substance and an animal without the administration of the test substance.

[8] A screening method for a substance having an anticancer activity and/or a cancer metastasis suppressing activity, the method comprising the steps of
administering a test substance to the animal model of spontaneous cancer metastasis according to any of the above [2] to [4],
administering luciferin to the animal after the start of the administration of the test substance,
recording a chemiluminescence image of the cell-inoculation site and/or a target organ of the animal after the administration of luciferin, and
comparing the chemiluminescence image of the cell-inoculation site and/or a target organ between the animal with the administration of the test substance and an animal without the administration of the test substance.

[9] A screening method for an anticancer substance, the method comprising selecting a substance that increases the expression of RECK (reversion-inducing-cysteine-rich protein with kazal motifs) in a cancer cell.

[10] The screening method according to the above [9], wherein the substance that increases the expression of RECK in a cancer cell is a substance that increases a Reck gene promoter activity in a cancer cell.

[11] The screening method according to the above [10], wherein the method uses a cell provided with a reporter system containing a Reck gene promoter and a reporter gene and with a $HRAS^{12V}$ oncogene controlled by a tetracycline-inducible expression system.

[12] The screening method according to the above [11], wherein the cell provided with a reporter system containing a Reck gene promoter and a reporter gene and with a $HRAS^{12V}$ oncogene controlled by a tetracycline-inducible expression system is a CREF cell line derivative having a $HRAS^{12V}$ oncogene controlled by a Tet-off system, a 4.1-kb upstream fragment of a mouse Reck gene as the Reck gene promoter, a secreted alkaline phosphatase gene as the reporter gene, a neomycin resistance gene and a blasticidin S resistance gene.

[13] A mammalian cell provided with a reporter system containing a Reck gene promoter and a reporter gene and with a $HRAS^{12V}$ oncogene controlled by a tetracycline-inducible expression system.

[14] The mammalian cell according to the above [13], which is a CREF cell line derivative provided with a reporter system containing a Reck gene promoter and a reporter gene and with a $HRAS^{12V}$ oncogene controlled by a tetracycline-inducible expression system,
the CREF cell line derivative having a $HRAS^{12V}$ oncogene controlled by a Tet-off system, a 4.1-kb upstream fragment of a mouse Reck gene as the Reck gene promoter, a secreted alkaline phosphatase gene as the reporter gene, a neomycin resistance gene and a blasticidin S resistance gene.

[15] An anticancer drug comprising as an active ingredient a compound obtained by the screening method according to any of the above [9] to [12] or a pharmaceutically acceptable salt thereof, the compound being one selected from the group consisting of disulfuram, pyrithione, thimerosal, doxorubicin, camptothecine (s, +), gramicidin, daunorubicin, cephaeline, mechlorethamine, emetine, mitoxantrone, diaziquone, haloprogin, lycorine, methotrexate, paclitaxel, menadione, albendazole, meclocycline, demeclocycline, minocycline, podophyllotoxin, harmine, pyrimethamine, trimeprazine, cycloheximide, perhexyline, triamterene, triflupromazine, raloxifene, piperlongumine, hycanthone, etoposide, and doxycycline.

[16] The screening method according to the above [7] or [8], wherein the substance that increases the expression of RECK, the substance being obtainable by the screening method according to any of the above [9] to [12], is used as the test substance.

[17] An anticancer drug comprising as an active ingredient a compound obtained by the screening method according to the above [7], [8] or [16] or a pharmaceutically acceptable salt thereof, the compound being one selected from the group consisting of disulfuram, harmine, pyrithione, gramicidin and lycorine.

[18] A cancer metastasis suppressor comprising as an active ingredient a compound obtained by the screening method according to the above [7], [8] or [16] or a pharmaceutically acceptable salt thereof, the compound being one selected from the group consisting of disulfuram, harmine, pyrithione, gramicidin and lycorine.

Advantageous Effects of Invention

The present invention can provide a cancer cell line to be used in a short-term evaluation of spontaneous metastasis. Inoculation of the cell line into an experimental animal can produce an animal model of spontaneous cancer metastasis. The animal model of spontaneous cancer metastasis can be used in a screening method to obtain a substance that can serve as an active ingredient in an anticancer drug or a cancer metastasis suppressor. The present invention can also provide a screening method for selecting a substance that increases the expression of RECK in a cancer cell and further provide a mammalian cell suitable for use in the screening method. The screening method for selecting a substance that increase the expression of RECK can be used to select a substance that can serve as an active ingredient in an anticancer drug. The screening method for selecting a substance that increases the expression of RECK is also useful as a primary screening of the screening method using the animal model of spontaneous cancer metastasis.

BRIEF DESCRIPTION OF DRAWINGS

FIG. 7 (B) is images showing the endogenous RECK protein expression-inducing activity in RZmet3 cells exposed to DSF, DXR, Gra and Pyt.

FIG. 7 (C) is images showing the endogenous RECK protein expression-inducing activity in A549 cells exposed to DSF, DXR, Gra and Pyt.

FIG. 7 (D) is images showing the endogenous RECK protein expression-inducing activity in SW480 cells exposed to DSF, DXR, Gra and Pyt.

FIG. 7 (E) is images showing the endogenous RECK protein expression-inducing activity in RM72 cells exposed to DSF, DXR, Gra and Pyt.

FIG. 8 (B) is images showing the endogenous RECK protein expression-inducing activity in RM72 cells exposed to DSF, DXR, Gra and Pyt.

FIG. 9 (B) is a chart showing the comparison of spreading of RZmet3 cells incubated in the absence or presence of DSF for 24 hours.

FIG. 9 (C) is a chart showing the comparison of the relative speed of random migration of RZmet3 cells incubated in the absence or presence of DSF for 24 hours.

FIG. 17 (B) is a scattering diagram of the lung metastasis and tumor size of the individuals in a vehicle group, a Pyt group and a Hr group, showing the anti-tumorigenic and anti-metastatic activities of Pyt and Hr on a mouse model of spontaneous lung metastasis inoculated with RM72 cells.

FIG. 17 (C) is a chart of the relative tumor size and relative lung metastasis of Gra and Lyc groups compared to those in a vehicle group, showing the anti-tumorigenic and anti-metastatic activities of Gra and Lyc on a mouse model of spontaneous lung metastasis inoculated with RM72 cells.

FIG. 17 (D) is a scattering diagram of the lung metastasis and tumor size of the individuals in a vehicle group, a Gra group and a Lyc group, showing the anti-tumorigenic and anti-metastatic activities of Gra and Lyc on a mouse model of spontaneous lung metastasis inoculated with RM72 cells.

DESCRIPTION OF EMBODIMENTS

RM72 Cell

Figure 1:
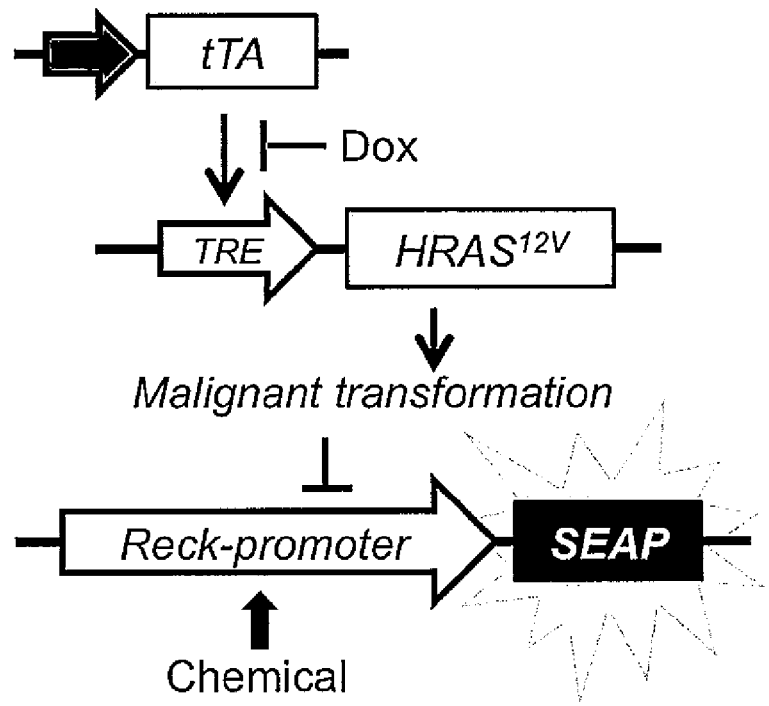
FIG. 1 is a chart showing foreign genes contained in YM3 cells.

The present invention provides a cell line RM72 (deposited with International Patent Organism Depositary, Incorporated Administrative Agency National Institute of Technology and Evaluation (2-5-8 Kazusakamatari, Kisarazu-shi, Chiba, 292-0818 Japan) under Accession No. NITE BP-1110 (Accession date: Jun. 22, 2011)). The RM72 cell line is derived from a human fibrosarcoma cell line, HT1080 (ATCC #CCL-121), and established by transfecting HT1080 cells with plasmids expressing neo (*Escherichia coli*-derived kanamycin resistance gene) and Hygro (*Escherichia coli*-derived hygromycin B resistance gene) as selective markers and with a plasmid expressing Luc (firefly luciferase gene) (see Example 1 (2)). After subcutaneous inoculation into nude mice, RM72 cells show tumor formation and within two weeks spontaneous lung-metastasis can be observed.

RM72 cells can be cultured, for example, in a Dulbecco's modified Eagle's medium (DMEM) containing 10% fetal bovine serum at 37° C. in 5% $CO_2$. Preferably the medium is supplemented with penicillin (e.g. about 100 U/ml), streptomycin (e.g. about 100 μg/ml), hygromycin B (e.g. about 400 U/ml) and G418 (e.g. about 100 mg/ml).

Animal Model of Spontaneous Cancer Metastasis and Production Method Therefor

The animal model of spontaneous cancer metastasis of the present invention may be any animal as long as it bears a RM72 cell-derived tumor. The animal model of spontaneous cancer metastasis of the present invention is highly useful in that it allows simultaneous evaluation of tumorigenesis and spontaneous cancer metastasis. In addition, the animal model is excellent in that it allows the evaluation of spontaneous cancer metastasis in a short period of time (about two weeks) after the subcutaneous inoculation of cells, not requiring a long period of time (40 to 100 days) for the evaluation as in a conventional method (Non Patent Literature 6). Further, since a luciferase expression vector has been introduced into RM72 cells, imaging of the location and volume of primary and metastatic foci can be achieved by recording chemiluminescence images of the animal's whole body after the administration of luciferin. That is, this animal model of spontaneous cancer metastasis is outstanding in that it allows the evaluation of tumorigenesis and spontaneous cancer metastasis without dissection.

The animal model of spontaneous cancer metastasis of the present invention can be produced by inoculating RM72 cells into an experimental animal. The experimental animal is not particularly limited and examples thereof include mammals such as mice, rats, hamsters, guinea pigs, rabbits, dogs, cats and monkeys. Preferred are rodents such as mice, rats, hamsters and guinea pigs and more preferred are mice. Preferably the animal is an immunodeficient animal. Examples of the immunodeficient animal include nude mice, nude rats and SCID mice.

The inoculation site of RM72 cells is not particularly limited as long as it allows RM72 cells to easily form a tumor. In view of ease of inoculation and tumor formation, subcutaneous inoculation is preferable. Specifically, dorsal subcutaneous and abdominal subcutaneous inoculations are suitable. The number of RM72 cells to be inoculated can be determined as appropriate depending on the kind and size of the animal, the inoculation site, and the like. For subcutaneous inoculation into a nude mouse, for example, about 1 to $5 \times 10^6$ cells are suspended in about 100 µl of PBS and the suspension is inoculated into the mouse with a syringe. Examination of the absence or presence of tumor formation may be performed about 5 to 7 days after the inoculation. Usually a tumor about 3 mm in diameter is formed about 5 to 7 days after the inoculation. An animal in which tumor formation has been confirmed can be used as the animal model of spontaneous cancer metastasis.

Screening Method Using Animal Model of Spontaneous Cancer Metastasis

The screening method of the present invention may be any method as long as it comprises the Steps (1) to (3) described below. Use of the screening method of the present invention allows the obtainment of a substance having an anticancer activity (e.g. tumor growth suppression, tumor shrinkage, tumor disappearance, etc.), a substance having a cancer metastasis suppressing activity, and a substance having both activities.

(1) The step of administering a test substance to the animal model of spontaneous cancer metastasis of the present invention.
(2) The step of determining the tumor size in the cell-inoculation site and the number and/or size of metastatic foci in the target organ after the start of the administration of the test substance.
(3) The step of comparing the tumor size in the cell-inoculation site and the number and/or size of metastatic foci in the target organ between the animal with the administration of the test substance and an animal without the administration of the test substance.

In the above Step (1), the test substance is not limited and may be, for example, a nucleic acid, a peptide, a protein, a non-peptidic compound, a synthetic compound, a fermentation product, a cell extract, a cell culture supernatant, a plant extract, a mammalian tissue extract, a plasma, or the like. The test substance may be a novel substance or a known substance. The test substance may be in the form of a salt and such a salt may be a salt with a physiologically acceptable acid or base.

The dose of the test substance is not particularly limited and may be determined as appropriate based on publicly known literature, preliminary examinations, or the like. The route of administration is selected depending on the test substance and can be selected as appropriate from known administration routes such as oral administration, intravenous administration, intraperitoneal administration, subcutaneous administration, intramuscular administration, and intratumoral administration. The administration period, the intervals of administration, the timing of evaluation, the number of times of evaluation are also not particularly limited and may be determined as appropriate depending on the test substance in view of the advantage of the screening method of the present invention, which advantage is that evaluation of a tumor in the cell-inoculation site and of a metastatic focus can be performed without dissection of the animal about 2 weeks after the inoculation of RM72 cells into the animal. Preferably a negative control group (e.g. administration of vehicle) is provided in addition to a test substance-administration group. A positive control group to which a known anticancer substance has been administered may be provided.

In the above Step (2), the determination may be done at any time as long as it is after the start of the administration of the test substance. The determination may be done during the administration period of the test substance, at the end of the administration period, or after a particular period of time from the end of the administration period. The determination by chemiluminescence of RM72 cells as described below does not require dissection of the animal and thus can be repeated multiple times. The method for determining the size of a tumor in the cell-inoculation site is not particularly limited. Examples thereof include a method in which the length, width, height, etc. of a tumor are measured with a vernier caliper etc. and the tumor volume is calculated, a method in which a tumor is harvested and weighed, and the like. The method for determining the number or size of metastatic foci in the target organ is not particularly limited. Examples thereof include a method in which a target organ is harvested by dissection of an animal and the number or size of metastatic foci is measured with the naked eye or under a microscope, and the like. The target organ may be any organ as long as it is a potential target for metastasis from a tumor developed in the cell-inoculation site. Examples of the organ include lung, lymph node, liver, bone, brain, and the like. An especially preferred target organ is the lung, in which the occurrence of metastasis within two weeks after the cell inoculation has been confirmed.

Further, since a luciferase expression vector has been introduced into RM72 cells, in the above Step (2) the determination of the tumor size in the cell-inoculation site and of the number and/or size of metastatic foci in the target organ can be performed without dissection of the animal by recording chemiluminescence images of the cell-inoculation site and the target organ after the administration of luciferin to the animal. That is, in this case, the above Step (2) preferably contains the following Steps (2-1) and (2-2): (2-1) the step of administering luciferin to the animal after the start of the administration of the test substance, and (2-2) the step of recording chemiluminescence images of the cell-inoculation site and/or the target organ of the animal after the administration of luciferin.

As the luciferin to be administered to the animal, a marketed d-luciferin can be suitably used. A luciferin solution can be prepared by, for example, dissolving luciferin in PBS, physiological saline, or the like. The method and route of administration of luciferin are selected such that luciferin can reach the location of RM72 cells in the animal. Hence, preferred is systemic administration such as intraperitoneal administration, intravenous administration, and the like. The dose is not particularly limited and, in the case of systemic administration, is selected as appropriate, for example, from the range of about 40 to 80 mg/kg.

After the administration of luciferin, the chemiluminescence images of the cell-inoculation site and/or the target organ of the animal are recorded. The recording method for the chemiluminescence images may be any method as long as it can record the chemiluminescence images of the cell-inoculation site and/or the target organ of the animal, but preferably the chemiluminescence images of the whole body of the animal under anesthesia are recorded. The period of time from luciferin administration till recording of the chemiluminescence images is not particularly limited. However, for example, in the case of intraperitoneal administration, the clearance time is considered to be about 30 minutes and therefore recording is preferably done within 30 minutes after luciferin administration. More preferred is within about zero to 20 minutes after luciferin administration. Recording of the chemiluminescence images of the whole body can be performed with a marketed in vivo optical imaging system (e.g. IVIS Imaging System (Xenogen) etc.). The obtained images can be analyzed with a marketed image analysis software (e.g. Living Image software (Xenogen) etc.).

In the above Step (3), the tumor size in the cell-inoculation site and the number and/or size of metastatic foci in the target organ are compared between the animal with the administration of the test substance and an animal without the administration the test substance. As the animal without the administration of the test substance, the negative control group (e.g. a vehicle-administration group) is usually applicable.

A test substance can be determined to have an anticancer activity (e.g. tumor growth suppression, tumor shrinkage, tumor disappearance, etc.) when the tumor size of the animal with the administration of the test substance is smaller than that of an animal without the administration of the test substance. Preferably a test substance that decreases the size of a tumor to 50% or less, more preferably 10% or less, is defined as an anticancer substance.

In addition, a test substance can be determined to have a cancer metastasis suppressing activity when the number of metastatic foci in the target organ of the animal with the administration of the test substance is smaller than that of an animal without the administration of the test substance. Further, a test substance can be determined to have a cancer metastasis suppressing activity when the size of a metastasis focus in the target organ of the animal with the administration of the test substance is smaller than that of an animal without the administration of the test substance. Preferably a test substance that decreases the number or size of metastasis foci to 20% or less, more preferably 5% or less, is defined as a cancer metastasis suppressing substance.

Screening Method for Selecting Substance that Increases the Expression of RECK in Cancer Cells The present invention provides a screening method for an anticancer drug, the method comprising selecting a substance that increases the expression of RECK in a cancer cell. The inventors' findings in the past regarding RECK (Non Patent literature 1, 2, 3, etc.) imply that RECK is useful as a prognosis marker and a promising target molecule for cancer therapy. Therefore, a substance that increases the expression of RECK in a cancer cell is considered to be useful as an active ingredient of an anticancer drug.

Examples of the screening method for an anticancer substance, the method comprising selecting a substance that increases the expression of RECK in a cancer cell, include a method comprising making a test substance in contact with a cultured cancer cell, measuring the amount of the RECK protein or mRNA in the cell, and analyzing the test substance-dependent changes in the amount of the RECK protein or mRNA, but not limited thereto.

The test substance is not limited and may be, for example, a nucleic acid, a peptide, a protein, a non-peptidic compound, a synthetic compound, a fermentation product, a cell extract, a cell culture supernatant, a plant extract, a mammalian tissue extract, a plasma, or the like. The test substance may be a novel substance or a known substance. The test substance may be in the form of a salt and such a salt may be a salt with a physiologically acceptable acid or base.

The RECK protein can be quantified, after extraction of the protein from cells through a known method, by a known protein quantitation method. Examples of the known protein quantitation method include Western blotting, EIA, ELISA, RIA, a method using a protein quantitation reagent, and the like. The RECK mRNA can be quantified, after extraction of the RNA from cells through a known method, by a known mRNA quantitation method. Examples of the known mRNA quantitation method include Northern blotting, RT-PCR, quantitative RT-PCR, RNase protection assay, and the like.

A method for analyzing the test substance-dependent changes in the amount of the RECK protein or mRNA is not particularly limited. For example, a test substance can be selected as a substance of interest when the amount of the RECK protein or mRNA in a cell made in contact with the test substance increases compared to that in a control group free from the contact with the test substance. The degree of increase in the amount of the RECK protein or mRNA by a test substance is not particularly limited. For example, preferred is a test substance that increases the amount of the protein or mRNA to 150% compared to the amount in cells free from the contact with the test substance, and more preferred is a test substance that increases the amount of the protein or mRNA to 175% or more.

The inventors have established a cell line for efficient screening for a substance that increases the expression of RECK in a cancer cell. This cell line is provided with a reporter system containing a Reck gene promoter and a reporter gene and with a $HRAS^{12V}$ oncogene controlled by a tetracycline-inducible expression system. The cell line exhibits cancer cell morphology or normal cell morphology depending on the absence or presence of tetracycline. Hence, the cell line is suitable for the screening method of the present invention because it allows easy comparison of the RECK expression-inducing activity in a cancer cell and a normal cell.

With the use of the cell line provided with a reporter system containing a Reck gene promoter and a reporter gene and with a $HRAS^{12V}$ oncogene controlled by a tetracycline-inducible expression system, a test substance can be determined to be a substance of interest when the expression of the reporter gene in the cells made in contact with the test substance increases compared to the expression in the cells in cancer cell morphology which is free from the contact with the test substance. When the cells in the two different phenotypes, cancer cell morphology and normal cell morphology, induced by the absence or presence of tetracycline are made into contact with a test substance, the expression of the reporter gene in both types of the cells may be comparable but preferably the expression in the cells with cancer morphology is higher. More preferably the expression of the reporter gene in the cells with cancer morphology is 1.5-fold higher or more than that in the cells with normal morphology, further more preferably 2-fold higher or more.

In particular, the cell line that the inventors have established is a cell line derived from a CREF cell line (rat fibroblast cell line; reference: Fisher P B, Babiss L E, Weinstein I B, Ginsberg H S. Analysis of type 5 adenovirus transformation with a cloned rat embryo cell line (CREF). Proc Natl Acad Sci USA 1982; 79: 3527-3531.) and the cell line has a $HRAS^{12V}$ oncogene controlled by a Tet-off system, a 4.1-kb upstream fragment of a mouse Reck gene as a Reck gene promoter, a secreted alkaline phosphatase gene as a reporter gene, a neomycin resistance gene and a blasticidin S resistance gene. The cell line can be produced by the method described in Example 1 (1). The inventors selected, from the cells produced by the method described in Example 1 (1), one clone that had shown the highest degree of SEAP up-regulation after treatment with a tetracycline antibiotic doxycycline, and named this cell line YM3 and used for the screening method. Thus, the YM3 cell line is especially suitable for efficient screening for a substance that increases the expression of RECK in a cancer cell.

The inventors have employed a secreted alkaline phosphatase (SEAP) gene as a reporter gene but the reporter gene is not limited thereto. Any commonly used reporter gene can be suitably employed. Preferred is a stable reporter gene whose activity is easy to quantify. Examples of such a reporter gene include a gene encoding luciferase, β-galactosidase, β-glucuronidase, chloramphenicol acetyltransferase, alkaline phosphatase, peroxidase, green fluorescent protein (GFP), or the like.

The inventors have employed a 4.1-kb upstream region of a mouse Reck gene (Gene ID: 53614, Chromosome 4—NC_000070.5 43884251-43888453) as a Reck gene promoter, but the Reck gene promoter is not limited thereto. Any Reck gene promoter of other mammals can also be suitably employed. Examples of the mammals include human, chimpanzee, monkey, dog, cattle, rat, guinea pig, and the like and preferred is human. The base sequences of the Reck gene promoter region of various kinds of animals can be obtained from a known database (DDBJ, GenBank, EMBL etc.). For example, a human RECK gene promoter region is represented by Gene ID: 8434, Chromosome 9—NC_000009.11 36,032,644-36,036,971.

The inventors have employed a $HRAS^{12V}$ oncogene controlled by a Tet-off system but a $HRAS^{12V}$ oncogene controlled by a Tet-on system can also be employed. An expression-inducing system using a drug other than tetracycline may be employed. Examples of such an expression-inducing system include a method using a dexamethasone-MMTV promoter system or a Cre-loxP recombination system, and the like.

The inventors have employed a neomycin resistance gene and a blasticidin S resistance gene as selective markers but the selective marker is not limited thereto. Any known selective marker that is applicable to a mammalian cell can be suitably employed. Specifically, examples thereof include puromycin, hygromycin B, zeocin, and the like.

The present invention encompasses the above suitable cell line for efficient screening for a substance that increases the expression of RECK in a cancer cell. That is, the present invention also encompasses a mammalian cell provided with a reporter system containing a Reck gene promoter and a reporter gene and with a $HRAS^{12V}$ oncogene controlled by a tetracycline-inducible expression system. More preferably, the cell is a CREF cell line-derived mammalian cell provided with a reporter system containing a Reck gene promoter and a reporter gene and with a $HRAS^{12V}$ oncogene controlled by a tetracycline-inducible expression system, the CREF cell line derivative having a $HRAS^{12V}$ oncogene controlled by a Tet-off system, a 4.1-kb upstream fragment of a mouse Reck gene as the Reck gene promoter, a secreted alkaline phosphatase gene as the reporter gene, a neomycin resistance gene and a blasticidin S resistance gene.

The present screening method for selecting a substance that increases the expression of RECK in a cancer cell is suitable for prescreening for a test substance that is to be subjected to a screening method using the above animal model of spontaneous cancer metastasis.

Pharmaceutical Comprising Compound Obtained by Screening Method of the Present Invention as Active Ingredient A substance that increases the expression of RECK selected by the screening method of the present invention is useful as an active ingredient of a Reck activator, an anticancer drug, or a cancer metastasis suppressor; an active ingredient candidate; or a leading compound. The inventors screened a 880-member chemical library using the screening method of the present invention and selected 34 compounds that activate a Reck gene promoter in a dose-response manner. In particular, selected are disulfuram, pyrithione, thimerosal, doxorubicin, camptothecine (s, +), gramicidin, daunorubicin, cephaeline, mechlorethamine, emetine, mitoxantrone, diaziquone, haloprogin, lycorine, methotrexate, paclitaxel, menadione, albendazole, meclocycline, demeclocycline, minocycline, podophyllotoxin, harmine, pyrimethamine, trimeprazine, cycloheximide, perhexyline, triamterene, triflupromazine, raloxifene, piperlongumine, hycanthone, etoposide, and doxycycline, or a pharmaceutically acceptable salt thereof (see Tables 1 and 2 in Example 2). These compounds are considered to be useful as an active ingredient of a Reck activator, an anticancer drug, or a cancer metastasis suppressor. Therefore, the present invention provides a Reck activator, an anticancer drug, or a cancer metastasis suppressor that comprises as an active ingredient one selected from the group consisting of the 34 compounds or a pharmaceutically acceptable salt thereof.

Among the above 34 compounds, at least 5 compounds, disulfuram, harmine, pyrithione sodium salt, gramicidin, and lycorine, have been confirmed to have an anticancer activity (e.g. tumor growth suppression, tumor shrinkage, tumor disappearance, etc.) and a cancer metastasis suppressing activity by the screening method using the animal model of spontaneous cancer metastasis of the present invention. Therefore, the present invention provides an anticancer drug comprising as an active ingredient one selected from the group consisting of disulfuram, harmine, pyrithione, gramicidin and lycorine or a pharmaceutically acceptable salt thereof. The present invention also provides a cancer metastasis suppressor comprising as an active ingredient one selected from the group consisting of disulfuram, harmine, pyrithione, gramicidin and lycorine or a pharmaceutically acceptable salt thereof.

Examples of "a pharmaceutically acceptable salt" include a salt of alkali metals (e.g. potassium, sodium, lithium, etc.), a salt of alkaline earth metals (e.g. calcium, magnesium, etc.), an ammonium salt (e.g. a tetramethylammonium salt, a tetrabutylammonium salt, etc.), a salt of organic amines (e.g. triethylamine, methylamine, dimethylamine, cyclopentylamine, benzylamine, phenethylamine, piperidine, monoethanolamine, diethanolamine, tris(hydroxymethyl)methylamine, lysine, arginine, N-methyl-D-glucamine, etc.), and an acid addition salt (e.g. inorganic acid salts such as hydrochloride, hydrobromide, hydroiodide, sulfate, phosphate and nitrate; and organic acid salts such as acetate, trifluoroacetate, lactate, tartrate, oxalate, fumarate, maleate, benzoate, citrate, methanesulfonate, ethanesulfonate, benzenesulfonate, toluenesulfonate, isethionate, glucuronate and gluconate).

All the above 34 compounds are known compounds that are preparable by known methods and also commercially available. Among the 34 compounds, the compounds which exist as optical isomers, stereoisomers, regioisomers, rotamers, or the like may be either of two isomers of these kinds or a mixture thereof. The 34 compounds may be a hydrate or solvate or may be labeled with an isotope etc.

A pharmaceutical comprising as an active ingredient a compound obtained by the screening method of the present invention can be formulated by appropriately combining one compound selected from the group consisting of the above 34 compounds or of the above 5 compounds or a pharmaceutically acceptable salt thereof with a pharmaceutically acceptable carrier and an additive. In particular, such a pharmaceutical may be formulated into an oral formulation such as a tablet, a coated tablet, a pill, a powder, a granule, a capsule, a liquid, a suspension and an emulsion; or a parenteral formulation such as an injection, an infusion, a suppository, an ointment and a patch. The blending ratio of a carrier or an additive is determined as appropriate based on the range usually employed in the pharmaceutical field. The carrier or additive that can be combined is not particularly limited and examples thereof include various kinds of carriers such as water, physiological saline, other aqueous vehicles, aqueous or oily bases; and various kinds of additives such as excipients, binders, pH adjusting agents, disintegrants, absorption enhancers, lubricants, colorants, corrigents and flavors.

Examples of the additive that can be mixed into a tablet, a capsule, or the like include binders such as gelatin, corn starch, tragacanth and gum arabic; excipients such as crystalline cellulose; swelling agents such as corn starch, gelatin and alginic acid; lubricants such as magnesium stearate; sweeteners such as sucrose, lactose and saccharin; and flavors such as peppermint, a *Gaultheria adenothrix* oil and cherry. When the dosage unit form is a capsule, it may further contain, in addition to materials of the above type, a liquid carrier such as oil. An aseptic composition for injection can be formulated according to usual pharmaceutical practice, for example, by dissolving or suspending an active substance in a vehicle like water for injection, or a naturally occurring vegetable oil such as sesame oil and coconut oil. As an aqueous liquid for injection, for example, physiological saline or an isotonic solution containing glucose and/or other auxiliary agents (e.g. D-sorbitol, D-mannitol, sodium chloride, etc.) or the like is used and may be used in combination with a suitable solubilizing agent, for example, alcohol (e.g. ethanol), polyalcohol (e.g. propylene glycol, polyethylene glycol), a nonionic surfactant (e.g. polysorbate 80™, HCO-50), or the like. As an oily liquid, for example, sesame oil, soybean oil, etc. is used and may be used in combination with a solubilizing agent such as benzyl benzoate and benzyl alcohol. The above liquids may be combined with a buffer (e.g. phosphate buffer, sodium acetate buffer, etc.), a soothing agent (e.g. benzalkonium chloride, procaine hydrochloride, etc.), a stabilizer (e.g. human serum albumin, polyethylene glycol, etc.), a preservative (e.g. benzyl alcohol, phenol, etc.), an antioxidant, or the like.

A pharmaceutical thus obtained can be administered to, for example, a human or other mammals (e.g. rat, mouse, rabbit, sheep, pig, cattle, cat, dog, monkey, etc.). The dose, the frequency of administration, the intervals of administration, and the like are determined as appropriate depending on the conditions of the animal subject, the target cancer type, the symptoms, the method of administration, and the like.

The present invention includes the following aspects.

(a) A cancer therapy method comprising administering to a mammal an effective dose of one selected from the group consisting of the above 34 compounds or of the above 5 compounds or a pharmaceutically acceptable salt thereof or a pharmaceutically acceptable salt thereof.

(b) Use of one selected from the group consisting of the above 34 compounds or of the above 5 compounds or a pharmaceutically acceptable salt thereof for producing an anticancer drug.

(c) One selected from the group consisting of the above 34 compounds or of the above 5 compounds or a pharmaceutically acceptable salt thereof to be used in cancer therapy.

(d) A cancer metastasis suppressing method comprising administering to a mammal an effective dose of any of the above 5 compounds and a pharmaceutically acceptable salt thereof.

(e) Use of one selected from the group consisting of the above 5 compounds or a pharmaceutically acceptable salt thereof for producing a cancer metastasis suppressor.

(f) One selected from the group consisting of the above 5 compounds or a pharmaceutically acceptable salt to be used in cancer metastasis suppression.

EXAMPLES

The present invention will be illustrated below in more detail with reference to Examples but the present invention is not limited thereto.

Example 1

Figure 2:
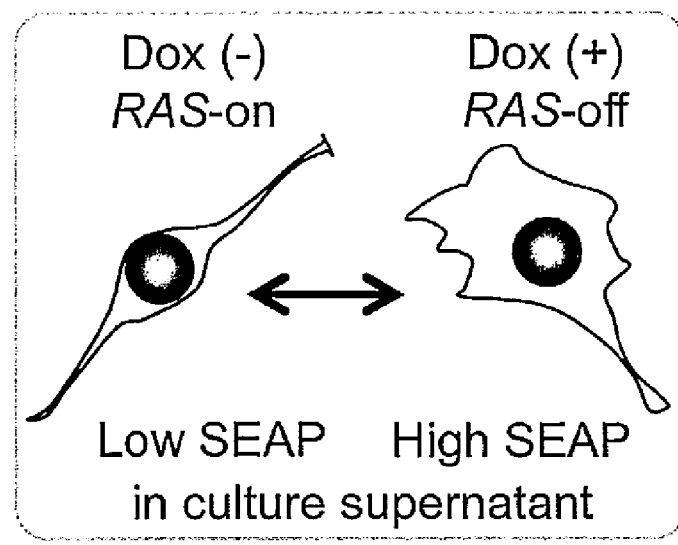
FIG. 2 is a chart showing a property of YM3 cells.

Establishment of Cell Line (1) Establishment of Cell Line with Reck Gene Promoter-Reporter System A 4.1-kb upstream region of a mouse Reck gene (Gene ID: 53614, Chromosome 4—NC_000070.5 43884251-43888453) was inserted into a pSEAP2-Basic vector (Clontech) to give a pSEAP-RP4.1 plasmid. The inventors also had previously established a cell line by stably transfecting a rat fibroblast cell line, CREF (Fisher P B, Babiss L E, Weinstein I B, Ginsberg H S. Analysis of type 5 adenovirus transformation with a cloned rat embryo cell line (CREF). Proc Natl Acad Sci USA 1982; 79: 3527-3531.), with two plasmids (a trans-repressor expression vector and a target vector) for expressing $HRAS^{12V}$ gene under the control of a tetracycline-inducible transactivator (Tet-off) system, and this cell line, TF323-C3 (G418 resistance), exhibits malignant phenotype via $HRAS^{12V}$ expression in a regular liquid medium and normal cell morphology via inhibition of $HRAS^{12V}$ expression in the presence of doxycycline (Dox; 2 μg/ml) (Sasahara R M, Takahashi C, Noda M. Involvement of the Sp1 site in ras-mediated downregulation of the RECK metastasis suppressor gene. Biochem Biophys Res Commun 1999; 264: 668-675.). The TF323-C3 cells were co-transfected with pSEAP-RP4.1 and pUCSV-BSD (ratio (w/w)=4:1) followed by selection in a growth medium containing 8 μg/ml blasticidin S (dual resistance to G418/blasticidin S). One clone which showed the highest degree of SEAP up-regulation after Dox treatment was selected to establish an intended cell line (named YM3) (see FIGS. 1 and 2). SEAP was up-regulated in YM3 cells also after treatment with hypothemycin (1 μg/ml), a MEK inhibitor inducing flat reversion in v-K-ras-transformed cells.

TF323-C3 cells can be distributed from one of the inventors Makoto Noda.

(2) Establishment of Spontaneous Metastasis Cell Line

A human fibrosarcoma-derived cell line, HT1080 (ATCC #CCL-121), was stably transfected with a plasmid containing a neo marker and subcutaneously transplanted into a nude mouse. About one month later a tumor that developed in an axillary lymph node was dissociated and cultured in a liquid medium containing G418 (1 mg/ml) and resulting colonies were separated to give a cell line RZmet3. RZmet3 cells show axillary lymph node metastasis about two weeks after subcutaneous inoculation. Next, RZmet3 cells were stably transfected with two plasmids, pGL4 (containing a *Photinus pyralis* luciferase gene; Promega) and pcDNA3.1(−)-Hygro (containing a hygromycin B phosphotransferase gene (resistance gene); Invitrogen), and recloned in a liquid medium containing G418 (1 mg/ml) and hygromycin B (400 U/ml), and clones that showed high levels of luciferase activity were separated. Among these clones, several clones that showed high levels of gelatinase activity were selected and subcutaneously transplanted into nude mice. One clone was found to show lung metastasis two weeks after the transplantation and was named RM72.

Example 2

SEAP Assay (1) Experimental Method

YM3 cells were seeded onto 96-well plates at $1 \times 10^4$ cells in 100 µl per well and incubation was performed for 5 hours to allow the cells to settle. A compound solution (500 µM, 1 µl) was added to the medium. The employed test compounds were those in the chemical library Prestwick Chemical Library (Prestwick Chemical, Illkirch, France), which is composed of 880 structurally diverse known bioactive compounds, dissolved in nano-pure grade dimethyl sulfoxide (DMSO; Wako). The biological mechanisms or pharmacological effects of these diverse compounds have experimentally been verified, and more than 85% of the compounds have been marketed either in the United States or in Europe as pharmaceuticals or supplements in a wide range of therapeutic area. A vehicle (DMSO, 1 µl) alone as a negative control and hypothemycin (HPM, 1 mg/ml) as a positive control were added to two wells per plate. Each sample was tested on two different plates (duplicate samples).

Figure 3:
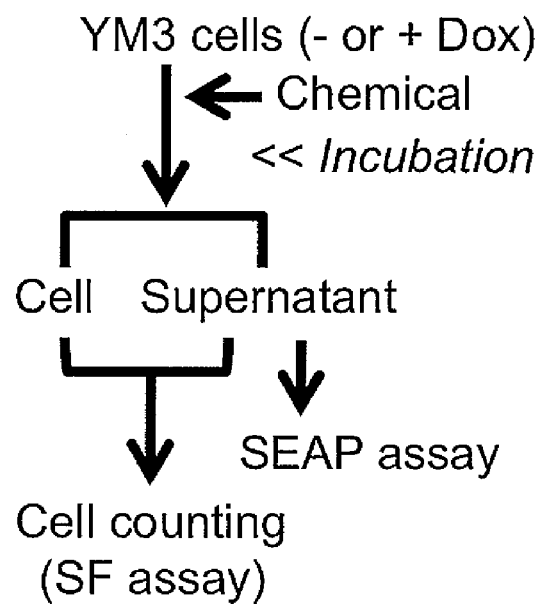
FIG. 3 is a chart showing the outline of a secreted alkaline phosphatase (SEAP) assay.

After incubation for 48 hours, a portion (10 µl) of the culture supernatant was sampled, incubated at 65° C. (heat treatment) for 30 minutes, and then subjected to the SEAP assay using Great EscAPe™ SEAP Chemiluminescence Detection Kit (Takara Bio). The remaining medium and the cells were subjected to the cell-counting assay using SF reagent. That is, SF reagent (Nacalai) (10 µl per well) was added to the medium, the plates were incubated for 3 hours in a $CO_2$ incubator, and the absorbance at 450 nm ($A_{450}$) was measured to obtain relative cell numbers. For the SEAP activity data, "SEAP measured value/$A_{450}$ value" was defined as "SEAP activity per cell", and the value obtained by dividing "SEAP activity per cell" of each compound by "SEAP activity per cell" of the negative control was defined as "relative SEAP activity". The mean "relative SEAP activity" of the duplicate samples and the standard error thereof were determined. For the cell number data, the value obtained by dividing the SF measured value of each compound by the SF measured value of the negative control was defined as "relative cell number", and the mean value of the duplicate samples and the standard error thereof were determined. Samples with a large standard error were tested again. In the experiment, duplicate samples were prepared each in a regular liquid medium and in a liquid medium containing Dox (2 µg/ml), and four mean values (the relative cell number and the relative SEAP activity in the Ras-ON state and the relative cell number and the relative SEAP activity in the Ras-OFF state) were obtained (see FIG. 3).

(2) Results

Figure 4:
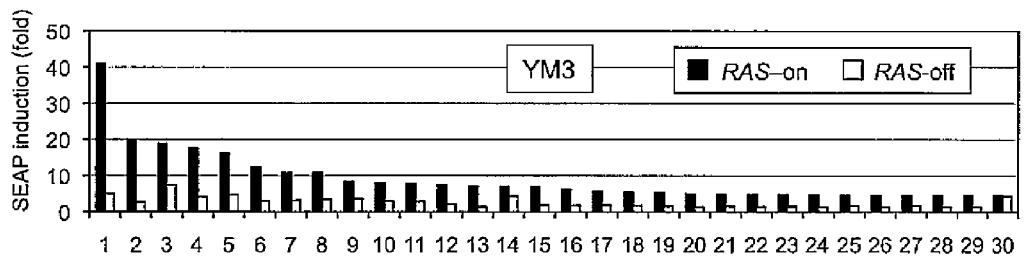
FIG. 4 is a chart showing some of the compounds that exhibited higher Reck gene promoter activities than HPM (a positive control) in a SEAP assay on a 880-member chemical library.

In the chemical library composed of 880 known biologically active low molecular compounds, 151 compounds were found to exhibit higher activities than HPM, a positive control. The positive control, HPM, is a drug which typically up-regulates the SEAP activity about twofold by inhibiting MEK. As shown in FIG. 4, in most cases, the extent of SEAP up-regulation was higher in transformed cells than that in non-transformed cells with a few exceptions, such as the 30th compound chlorhexidine.

Next, secondary screening was performed to investigate the dose-response activities of the 151 compounds. Thirty-four compounds were selected as positive samples as shown in Table 1. Among these, 4 compounds are tetracycline analogues (Table 1, ¶ in the Class column) and the levels of their activities (2.5- to 2.6-fold) showed little difference from that of Dox (1.96-hold). These tetracycline analogues probably activate the Reck promoter by inhibiting the expression of the Tet-off-HRAS$^{12V}$ gene inserted into YM3 cells, which conclusion is supported by the lack of the activity in the presence of Dox. The other 30 compounds could be classified into 7 categories and "others" (see Table 2), and it turned out that 10 compounds were classified into "anticancer drugs", which represents the greatest proportion (proportion: 10/34=29%). Since the original library contained 18 anticancer drugs (proportion: 18/880=2%), this screening provided about 15-fold enrichment.

TABLE 1

Top-34 chemicals selected using the YM3 assay

| Rank | Chemical[1] | Optimal conc. (µM)[2] | Induction (fold) | Activity in Dox[3] | Class[4] |
|---|---|---|---|---|---|
| 1 | Disulfiram [DSF] | 1.67 | 18.0 | + | I |
| 2 | Pyrithione sodium salt [Pyt] | 1.67 | 17.5 | + | V |
| 3 | Thimerosal | 5.00 | 9.33 | + | V |
| 4 | Doxorubicin hydrochloride [DXR] | 5.00 | 8.55 | + | II* |
| 5 | Camptothecine (S, +) | 5.00 | 7.71 | + | II |
| 6 | Gramicidin [Gra] | 5.00 | 7.30 | + | IV |
| 7 | Daunorubicin hydrochloride | 1.67 | 6.22 | + | II* |
| 8 | Cephaeline dihydrochloride heptahydrate | 5.00 | 5.61 | + | VII |
| 9 | Mechlorethamine hydrochloride | 5.00 | 4.98 | ± | II* |
| 10 | Emetine dihydrochloride | 1.67 | 3.79 | − | VII |

TABLE 1-continued

Top-34 chemicals selected using the YM3 assay

| Rank | Chemical[1] | Optimal conc. (μM)[2] | Induction (fold) | Activity in Dox[3] | Class[4] |
|---|---|---|---|---|---|
| 11 | Mitoxantrone dihydrochloride | 0.556 | 3.60 | + | II* |
| 12 | Diaziquone | 5.00 | 3.54 | ± | II |
| 13 | Haloprogin | 5.00 | 3.48 | + | V |
| 14 | Lycorine hydrochloride | 5.00 | 3.44 | + | VII |
| 15 | Methotrexate | 5.00 | 3.42 | ± | II* |
| 16 | Paclitaxel | 5.00 | 3.32 | ± | II* |
| 17 | Menadione | 5.00 | 3.21 | + | VIII |
| 18 | Albendazole | 1.67 | 2.89 | ± | VI |
| 19 | Meclocycline sulfosalicylate | 0.0617 | 2.59 | − | IV¶ |
| 20 | Demeclocycline hydrochloride | 1.67 | 2.57 | − | IV¶ |
| 21 | Minocycline hydrochloride | 0.556 | 2.54 | − | IV¶ |
| 22 | Podophyllotoxin | 5.00 | 2.48 | ± | VIII |
| 23 | Harmine hydrochloride | 5.00 | 2.44 | ± | VIII |
| 24 | Pyrimethamine | 5.00 | 2.33 | ± | III |
| 25 | Trimeprazine tartrate | 5.00 | 2.30 | − | VIII |
| 26 | Cycloheximide | 5.00 | 2.29 | ± | IV |
| 27 | Perhexiline maleate | 5.00 | 2.28 | + | VIII |
| 28 | Triamterene | 5.00 | 2.25 | − | VIII |
| 29 | Triflupromazine hydrochloride | 0.0617 | 2.18 | − | VIII |
| 30 | Raloxifene hydrochloride | 0.556 | 2.17 | − | II* |
| 31 | Piperlongumine | 5.00 | 2.06 | − | VIII |
| 32 | Hycanthone | 5.00 | 2.02 | + | VI |
| 33 | Etoposide | 5.00 | 1.99 | + | II* |
| 34 | Doxycycline hydrochloride | 0.185 | 1.96 | − | IV¶ |

[1]Chemicals selected for detailed studies are in bold letters, with their abbreviations in the parentheses.
[2]Optimal concentration determined by dose-response assays (dosages: 0.0617, 0.185, 0.556, 1.67, 5.00 μM) using YM3 cells.
[3]Activity in the presence of Dox (i.e., HRAS12V-off): +, more than 1.9-fold; ±, between 1.9 and 1.5-fold; −, less than 1.5-fold
[4]See Table 2.
*Included in FDA-Approved Oncology Drugs Set, Developmental Therapeutics Program, NCI
¶Tetracycline analogue

TABLE 2

Properties of the top-34 chemicals

| | Class | Chemical | Target of inhibition (application)/mode of action |
|---|---|---|---|
| I. | Alcohol deterrent | Disulfiram [DSF] | Aldehydodehydrogenase in hepatocyte, superoxide dismutase-1, chelation of zinc and copper cations |
| II. | Anticancer drugs | | |
| | Vinca alkaloid | Camptotnecine (S, +) | Topo I |
| | Podophyllum alkaloids | Etoposide | Topo II |
| | Anthracyclines | Doxorubicin [DXR] | DNA synthesis, Topo II |
| | | Daunorubicin | DNA synthesis, Topo II |
| | Nitrogen mustard | Mechlorethamine | DNA synthesis, Topo II |
| | DNA alkylator | Diaziquone | DNA synthesis |
| | Antibiotic | Mitoxantrone | DNA synthesis |
| | Taxane | Paclitaxel | Tubulin dissociation |
| | Hormone analogue | Raloxifene | Estrogen receptor |
| | Antimetabolite | Methotrexate | Dihydrofolate reductase |
| III. | Anti-malarial agent | Pyrimethamine | Dihydrofolate reductase |
| IV. | Anti-bacterial agents | | |
| | Antibiotic peptides | Gramicidin [Gra] | Cell membrane, phospholipid |
| | Piperidone | Cycloheximide | Protein synthesis, ribosome |
| | Tetracycline analogues | Demeclocycline | Protein synthesis, bacterial ribosome |
| | | Doxycycline | Protein synthesis, bacterial ribosome |
| | | Meclocycline | Protein synthesis, bacterial ribosome |
| | | Minocycline | Protein synthesis, bacterial ribosome |
| V. | Anti-fungal agents | Pyrithione sodium salt [Pyt] | Chelation of zinc cation |
| | | Haloprogin | Damaging fungal membrane |
| | | Thimerosal | Generation of ethyl-mercury |
| VI. | Anthelmintic agents | Albendazole | Tubulin polymerization |
| | | Hycanthone | RNA synthesis |
| VII. | Vomiting alkaloids | Cephaeline | Protein synthesis |
| | | Emetine | Protein synthesis |
| | | Lycorine | Protein synthesis |

TABLE 2-continued

Properties of the top-34 chemicals

| Class | | Chemical | Target of inhibition (application)/mode of action |
|---|---|---|---|
| VIII. | Others | Menadione (Vitamin K3) | ROS generation |
| | | Podophyllotoxin | Tubulin (antiwart, precursor of etoposide) |
| | | Trimeprazine (Alimemazine) | Histamine receptor, muscarinic acetylcholine receptor |
| | | Triflupromazine | Dopamine receptor, muscarinic acetylcholine receptor |
| | | Perhexiline | L-type calcium channel, Sodium/potassium ATPase, carnitine palmitoyltransferase-1 |
| | | Triamterene | Sodium/potassium ATPase |
| | | Harmine | Monoamine oxidase A |
| | | Piperlongumine | Thromboxane A2 receptor |

Example 3

Evaluation of Dose-Response Activity

Four compounds with a strong Reck gene promoter-inducing activity, disulfuram (hereinafter "DSF"; alcohol deterrent), doxorubicin (hereinafter "DXR"; anticancer drug), gramicidin (hereinafter "Gra"; antimicrobial agent) and pyrithione sodium salt (hereinafter "Pyt"; antifungal agent) were selected from different classes having different targets. Their dose-response activities in YM3 cells were evaluated.

Figure 5:
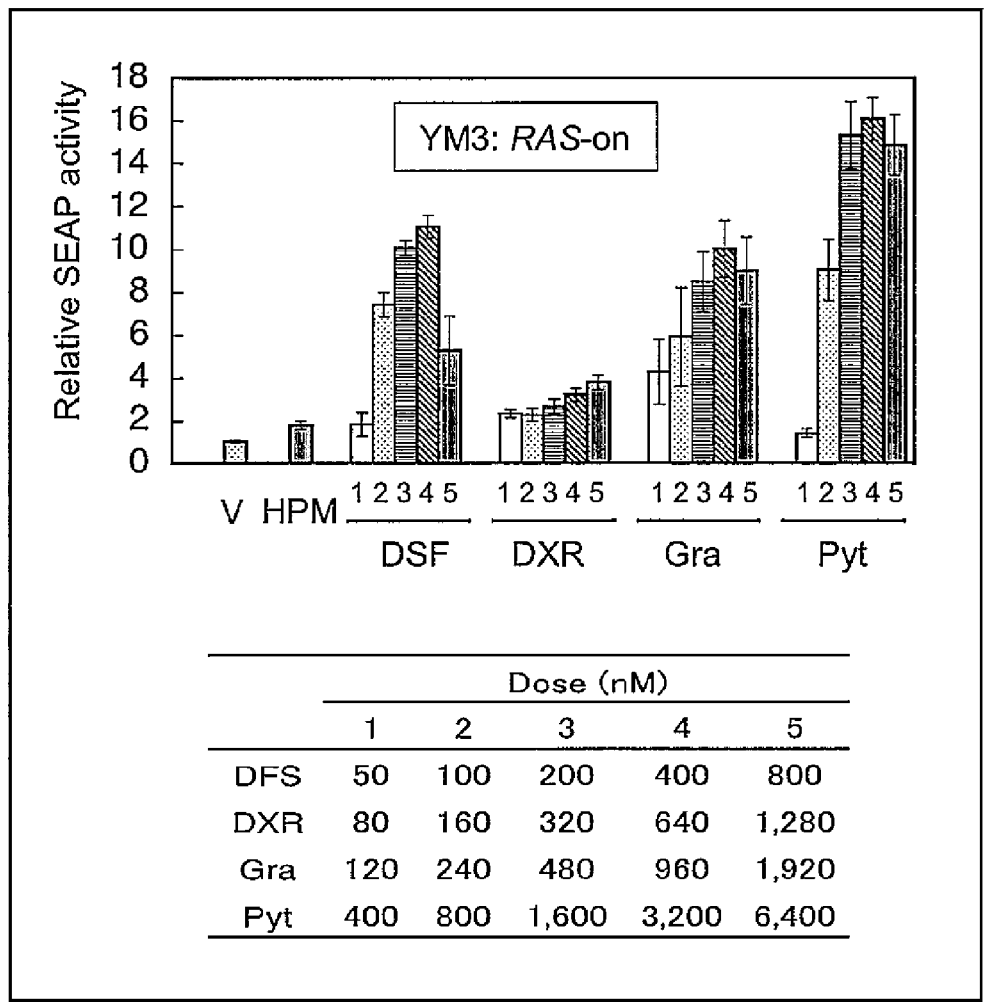
FIG. 5 is a chart showing the dose-response activities of four compounds with a strong Reck gene promoter-inducing activity, disulfuram (DSF), doxorubicin (DXR), gramicidin (Gra) and pyrithione sodium salt (Pyt), in YM3 cells.

The results are shown in FIG. 5. The concentration of each compound is shown in the table under the chart. The data of the negative control (V: 1% DMSO) and the positive control (HPM: 1 µg/ml) are also shown. The activities shown represent the mean±SEM (n=4).

Example 4

Evaluation of Reck-Luciferase Promoter Activity in HT1080 Cells

HT1080 cells stably transfected with pGL3-4110 were exposed to DSF, Pyt, DXR, or ammonium pyrrolidine dithiocarbamate (hereinafter "pDTC") at the doses indicted in FIG. 6 for 48 hours. Specifically, HT1080 cells stably transfected with pGL3-4110 were seeded onto a 96-well plate ($5 \times 10^4$ cells in 100 µl per well) and incubated for 24 hours, and 1 µl of each compound solution or a vehicle (DMSO) was added to each well. After incubation for 48 hours, the cells were lysed and the firefly luciferase activity in the cell lysate was measured using Steady-Glo Luciferase Assay Kit (Promega) and normalized per cell.

Figure 6:
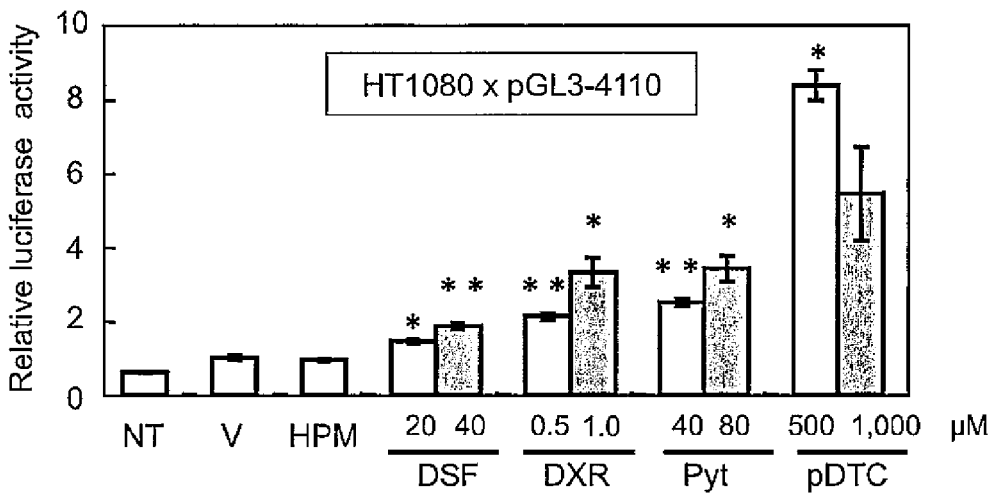
FIG. 6 is a chart showing luciferase activity as a measurement of the Reck gene promoter-inducing activity in HT1080 cells stably transfected with pGL3-4110 and exposed to DSF, Pyt, DXR or ammonium pyrrolidine dithiocarbamate (pDTC).
Figure 7A:
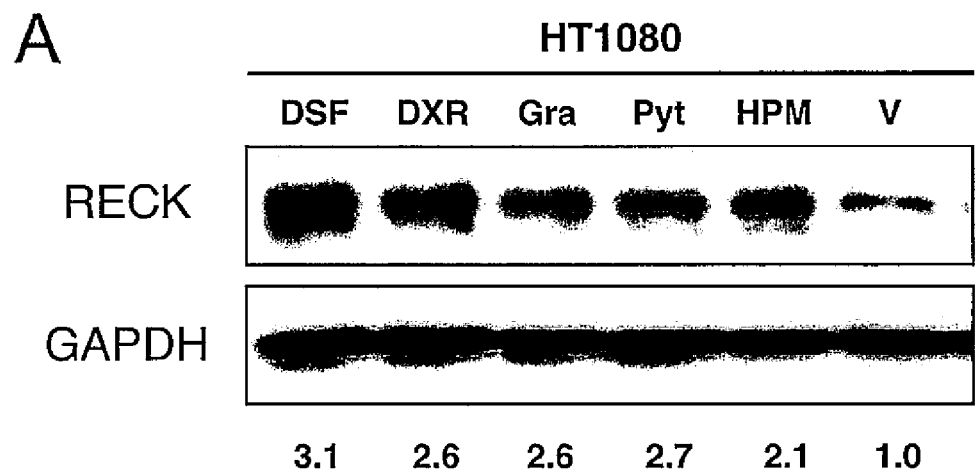
FIG. 7 (A) is images showing the endogenous RECK protein expression-inducing activity in HT1080 cells exposed to DSF, DXR, Gra and Pyt.
Figure 7B:
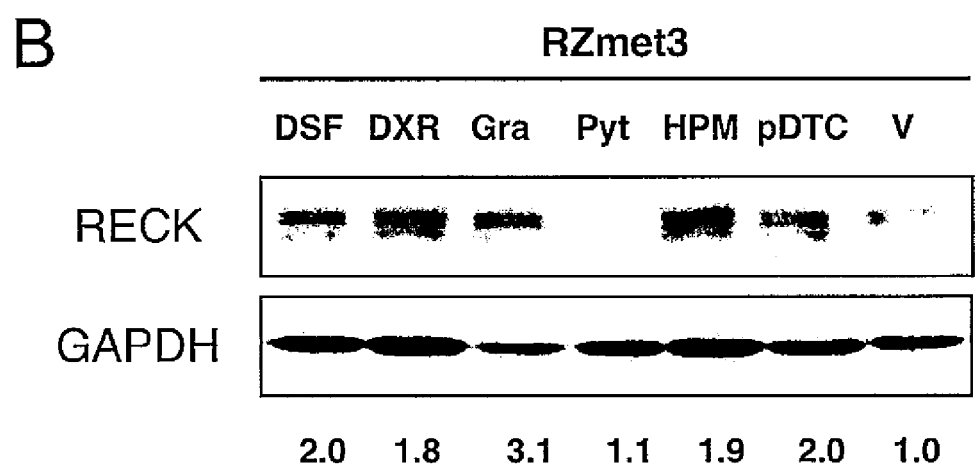
Figure 7C:
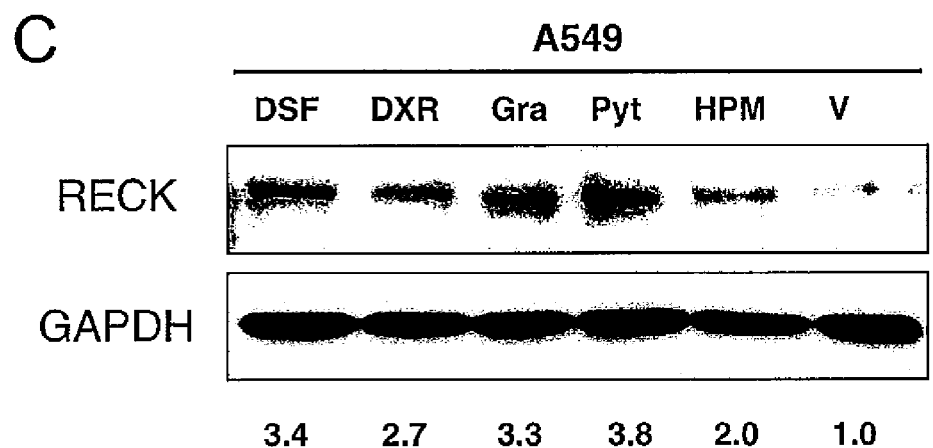
Figure 7D:
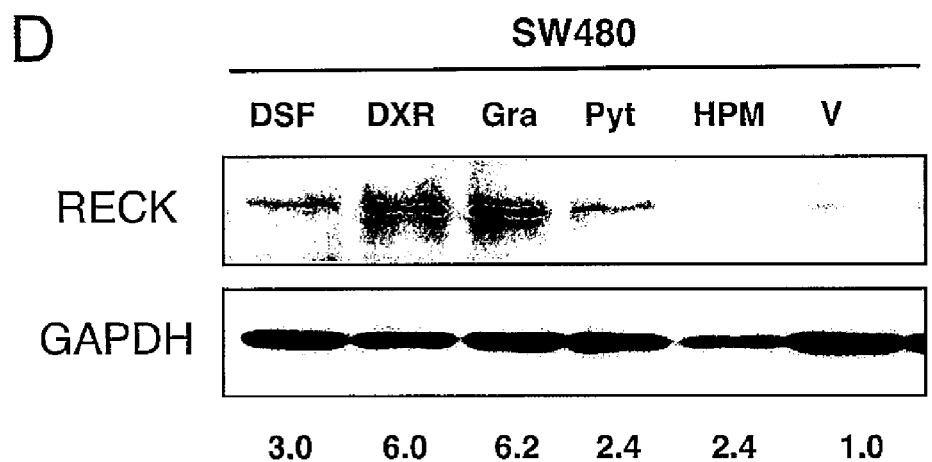
Figure 7E:
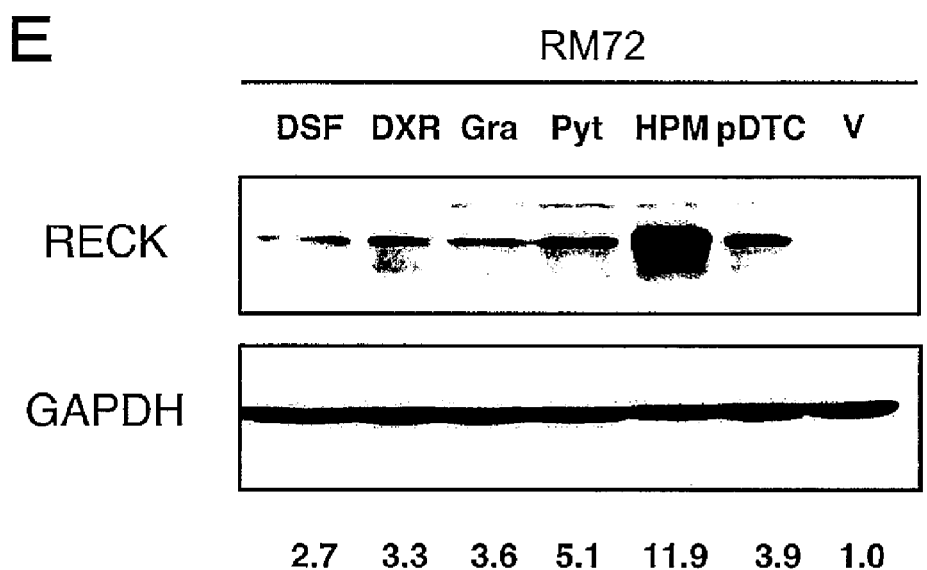

The results are shown in FIG. 6. The data of a no-treatment control (NT), a negative control (V: 1% DMSO) and a positive control (HPM: 1 µg/ml) are also shown. The activities shown represent the mean±SEM (n 4). Student's t-test compared with the vehicle (V)-treated cells was performed. * represents P<0.05 and ** represents P<0.01.

Example 5

Evaluation of Endogenous RECK Expression-Inducing Activity (1)

Five types of human malignant tumor-derived cell line, HT1080, RZmet3, A549 (human lung-adenocarcinoma cell), SW480 (human colon adenocarcinoma cell) and RM72 were exposed to DSF, DXR, Gra, and Pyt at $IC_{50}$ (RZmet3 and RM72 were also exposed to pDTC), 48 or 72 hours later the cells were lysed, and the expression of endogenous RECK protein was examined by immunoblotting. Specifically, the cells (cell density per 60-mm dish: HT1080 and A549, $5 \times 10^4$; RZmet3, $1 \times 10^5$; SW480, $1.5 \times 10^5$) were seeded in advance and exposed to each compound at $IC_{50}$ as determined by colony formation assay. HPM (1 µg/ml) as a positive control and 1% DMSO (vehicle) as a negative control were employed. The exposure time was 48 hours for HT1080, RZmet3 and RM72 and 72 hours for A549 and SW480. After incubation, the cell lysates were prepared and analyzed by immunoblot assay using an anti-RECK antibody (5B11D12), followed by stripping and reprobing with an anti-GAPDH antibody (6C5, Ambion). For visualization, Enhanced Chemiluminescence kit (Millipore) was used with a HRP-conjugated anti-mouse IgG-F (ab') monoclonal antibody (Cell Signaling) as a secondary antibody. Images were recorded and analyzed using LAS-3000 and MultiGauge software (FUJIFILM). Relative band intensities were obtained by normalization against GAPDH and subsequent division by the normalized value for the cells treated with the vehicle.

The results are shown in to FIGS. 7 (A) to (E). (A) shows the results for HT1080 cells, (B) shows the results for RZmet3 cells, (C) shows the results for A549 cells, (D) shows the results for SW480 cells, and (E) shows the results for RM72 cells. As is apparent from FIGS. 7 (A) to (E), all the compounds enhanced the expression of endogenous RECK in the human malignant tumor-derived cell line.

Example 6

Evaluation of Endogenous RECK Expression-Inducing Activity (2)

Of the 34 compounds selected by the secondary screening, lycorine (hereinafter "Lyc", vomiting alkaloid) and harmine (hereinafter "Hr", monoamine oxidase A) were evaluated for the endogenous RECK expression-inducing activity in RM72 cells. Specifically; RM72 cells under culture conditions were exposed to Lyc (1.3 µM) or Hr (11 µM) at concentrations equivalent to their $IC_{30}$ values for 48 hours and the expression of the RECK mRNA (RT-PCR assay) and the RECK protein (immunoblotting) were investigated. Relative band intensities were obtained by normalization against HPRT1 for the mRNA and against GAPDH for the protein and subsequent division by the normalized value for the cells treated with the vehicle.

Figure 8A:
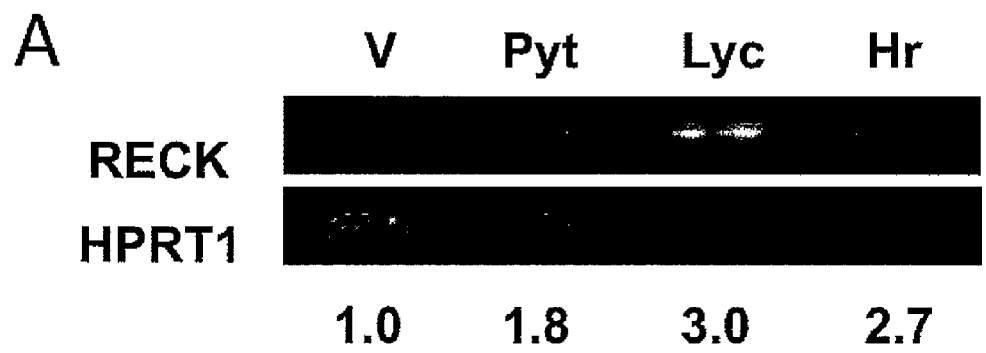
FIG. 8 (A) is images showing the endogenous RECK mRNA expression-inducing activity in RM72 cells exposed to lycorine (Lyc) and harmine (Hr).
Figure 8B:
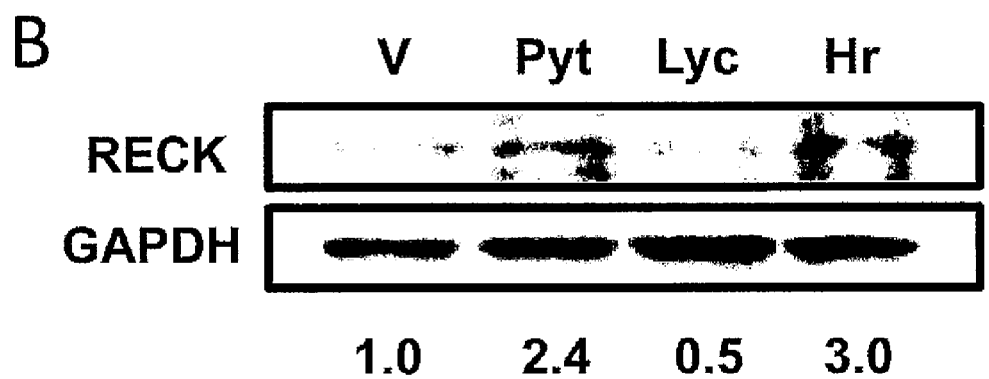

The results are shown in FIGS. 8 (A) and (B). (A) shows the results for the RECK mRNA and (B) shows the results for the RECK protein. As is apparent from FIGS. 8 (A) and (B), on the mRNA level both Lyc and Hr increased the expression of RECK but on the protein level Hr increased the expression and Lyc reduced the expression.

Example 7

Evaluation of Effects of DSF on Tumor Cells In Vitro

The morphology and behavior of RZmet3 cells in the absence or presence of DSF were investigated using time-lapse video-microscopy. Specifically, RZmet3 cells ($2 \times 10^4$ cells) seeded onto a 35-mm glass dish (IWAKI) were incubated for 24 hours, and the medium was replaced with a growth medium containing 10 μM DSF or 1% DMSO (vehicle). After incubation for 24 hours, the medium was replaced with Leibovitz's L-15 (GIBCO) containing 10% fetal bovine serum and 1% DMSO or 10 μM DSF. As described in literature (Morioka Y, Monypenny J, Matsuzaki T, Shi S, Alexander D B, Kitayama H, Noda M. The membrane-anchored metalloproteinase regulator RECK stabilizes focal adhesions and anterior-posterior polarity in fibroblasts. Oncogene 2009; 28: 1454-1464), the motility of the cells was recorded by time-lapse microscopy for 3 hours (3-minute interval). The speed of migration was calculated from a time series of coordinates (reference point; the center of the nucleus) using the Dunn's formula (Dunn G A. Characterising a kinesis response: time averaged measures of cell speed and directional persistence. Agents Actions Suppl 1983; 12: 14-33). Statistical significance was assessed by Student's t-test.

Figure 9A:
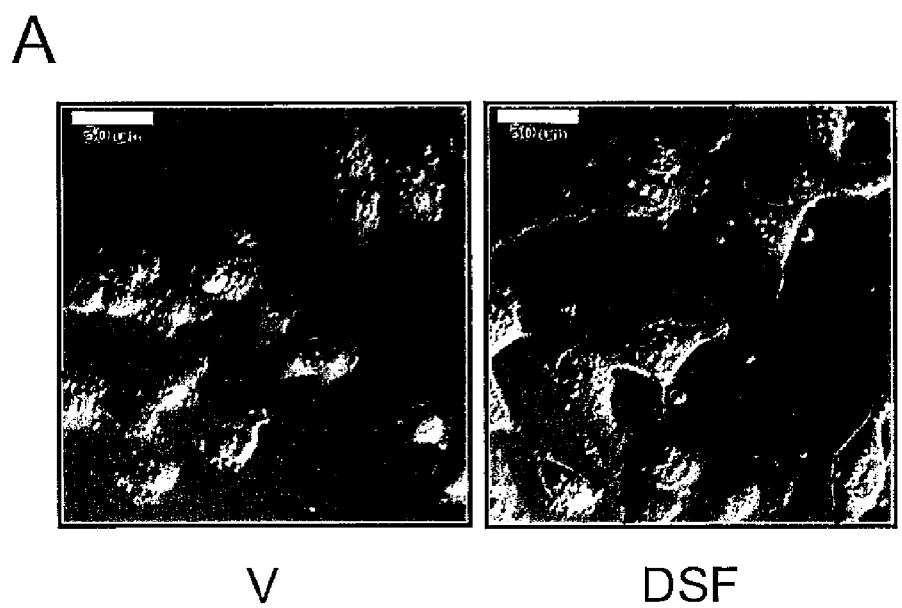
FIG. 9 (A) is differential interference contrast images of RZmet3 cells incubated in the absence or presence of DSF for 24 hours.
Figure 9B:
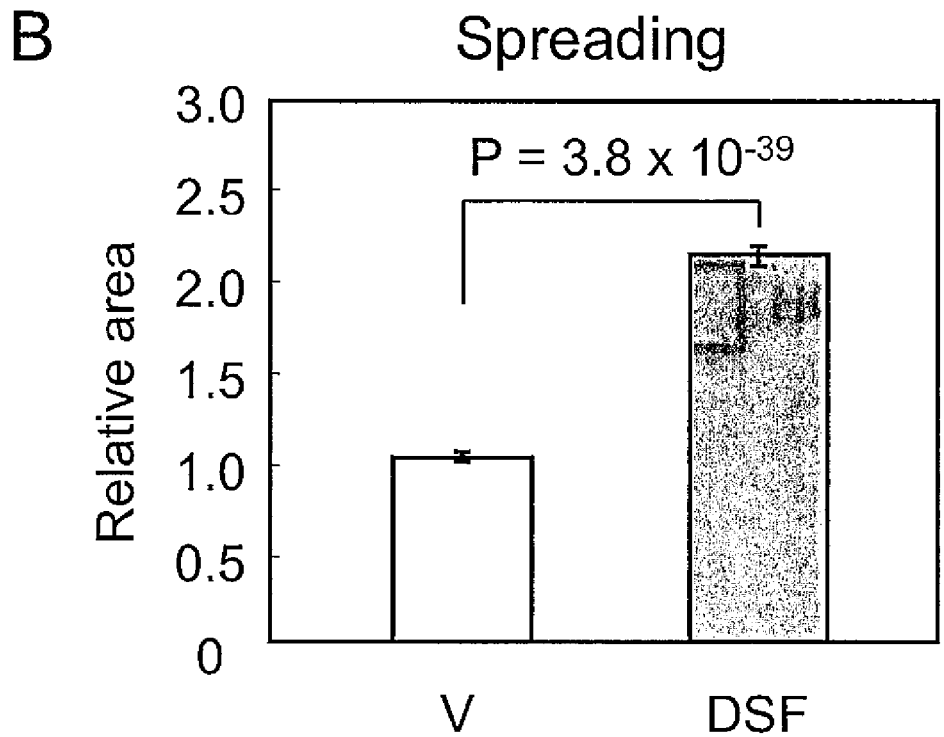
Figure 9C:
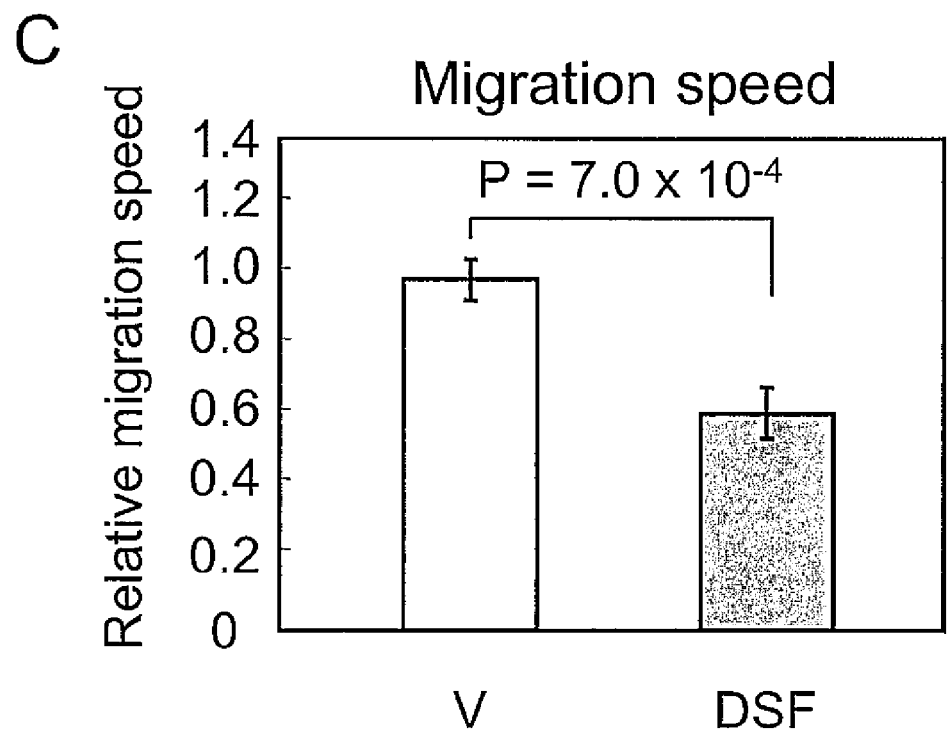

The results are shown in FIGS. 9 (A) to (C). (A) shows differential interference contrast images of RZmet3 cells incubated in the absence or presence of DSF for 24 hours, (B) shows the results of cell spreading presented as the ratio to a control (mean±SEM, n=100), and (C) shows the results of the relative speed of random migration (mean±SEM, n=10). As is apparent from FIGS. 9 (A) to (C), DSF induced flattening and spreading of RZmet3 cells and reduced the speed in random migration. These results are in accord with those of transfection of the RECK expression vector into the transformed cells.

Example 8

Gelatin Zymography

Gelatin zymography with the culture supernatant of RM72 cells treated with DSF, DXR, Gra, Pyt, pDTC, HPM, and DMSO (vehicle) was performed. Specifically, RM72 cells ($2 \times 10^4$ cells per well) seeded onto 96-well plates were incubated for 24 hours, and the medium was replaced with a medium containing each of the above compounds (DSF: 16 μM, DXR: 210 nM, Gra: 32 nM, Pyt: 5 μM, HPM: 1 μg/ml, pDTC: 20 μM). After incubated for 48 hours, the medium was replaced with 100 μl of DMEM containing 0.1% FBS and incubated for additional 12 hours. The culture supernatant was harvested, cleared of a solid matter by centrifugation, and analyzed by gelatin zymography in accordance with the method described in literature (Takahashi C, Sheng Z, Horan. T P, Kitayama H, Maki M, Hitomi K, Kitaura Y, Takai S, Sasahara R M, Horimoto A, Ikawa Y, Ratzkin B J, Arakawa T, Noda M. Regulation of matrix metalloproteinase-9 and inhibition of tumor invasion by the membrane-anchored glycoprotein RECK. Proc Natl Acad Sci USA 1998; 95: 13221-13226). The band intensities were normalized against the cell number determined by the SF assay.

Figure 10:
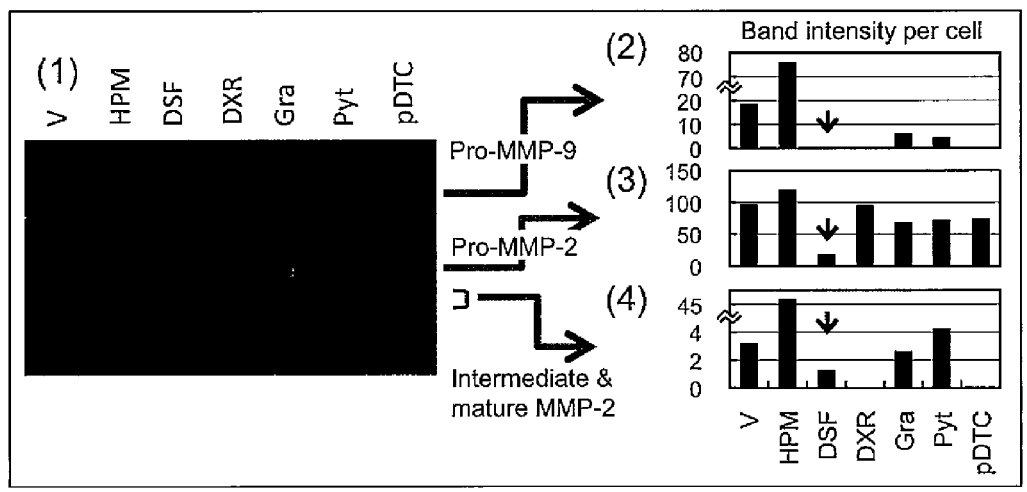
FIG. 10 is an image and charts showing gelatin zymography using the culture supernatant of RM72 cells treated with DSF, DXR, Gra or Pyt.

The results are shown in FIG. 10. The four compounds, DSF, DXR, Gra, and Pyt, reduced the pro-MMP-9 level in the culture supernatant. DSF also reduced the levels of pro-MMP-2 and intermediate/mature MMP-2.

Example 9

Evaluation of Anti-Tumorigenic and Anti-Metastatic Activities of DSF (1) Experimental Method RM72 cells ($3 \times 10^6$ cells) suspended in 0.1 ml of PBS were subcutaneously injected into the right posterior flank of Balb/c nude mice (6 weeks old, male, Charles River). Five days after the injection, the mice that developed small tumors (about 3 mm in diameter) were randomly divided into two groups (n=5 per group) and treated with DSF (50 mg/kg/day) dissolved in an olive oil or with an olive oil alone (vehicle) via intraperitoneal injection using 24-gauge needles. After 14-day treatment, the mice were anesthetized and their bioluminescence was recorded by the method described below. After the whole-body recording of the bioluminescence, the lung was resected, washed with PBS (−), and subjected to bioluminescence recording. The tumor size (length×width× height) was measured once a week. Statistical significance was assessed by Student's t-test.

(2) Recording Method of Bioluminescence

Mice under anesthesia were intraperitoneally injected with 75 mg/kg of d-luciferin dissolved in PBS (−). Bioluminescence images were acquired with IVIS ImagingSystem (Xenogen) at 5 minutes after the injection (Wang S, El-Deiry W S. Requirement of p53 targets in chemosensitization of colonic carcinoma to death ligand therapy. Proc Natl Acad Sci USA 2003; 100: 15095-15100; Minn A J, Kang Y, Serganova I, Gupta G P, Giri D D, Doubrovin M, Ponomarev V, Gerald W L, Blasberg R, Massague J. Distinct organ-specific metastatic potential of individual breast cancer cells and primary tumors. J Clin Invest 2005; 115: 44-55). The photons emitted from the whole bodies or the isolated organs were collected for a period of 60 seconds and integrated. The images were analyzed using Living Image software (Xenogen).

(3) Results

Figure 11:
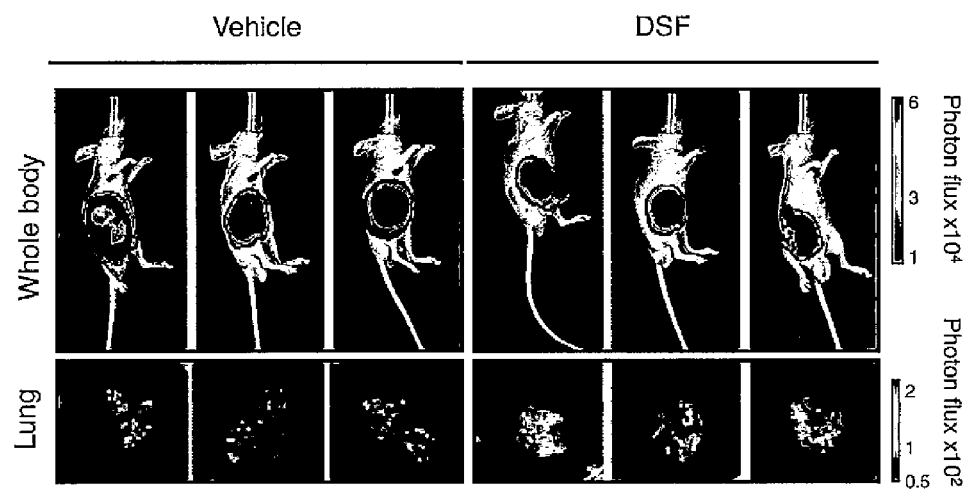
FIG. 11 is bioluminescence images of the whole bodies and lungs of a vehicle group and a DSF group, showing the anti-tumorigenic and anti-metastatic activities of DSF on a mouse model of spontaneous lung metastasis inoculated with RM72 cells.
Figure 12:
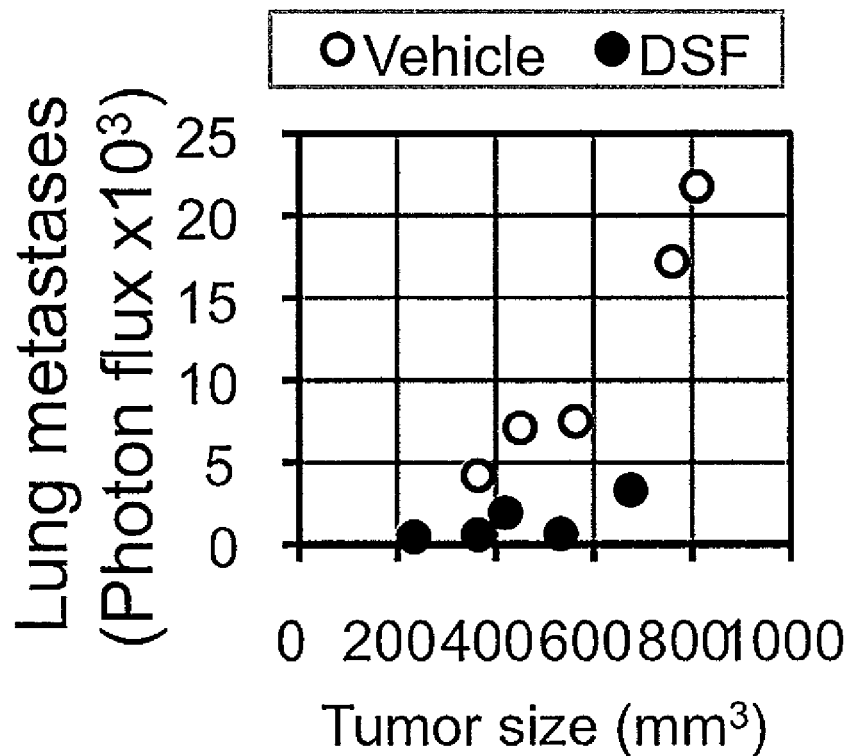
FIG. 12 is a scattering diagram of the lung metastasis and tumor size of the individuals in a vehicle group and a DSF group, showing the anti-tumorigenic and anti-metastatic activities of DSF on a mouse model of spontaneous lung metastasis inoculated with RM72 cells.
Figure 13:
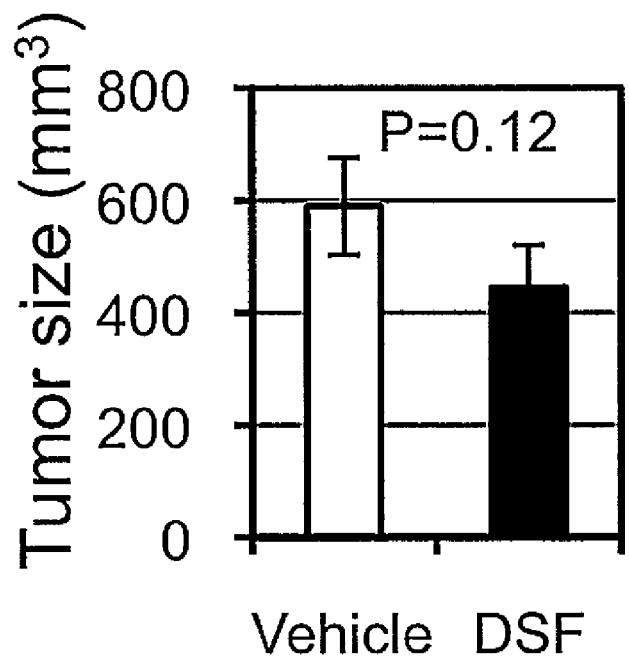
FIG. 13 is a chart of the comparison of the tumor size in a vehicle group and a DSF group, showing the anti-tumorigenic and anti-metastatic activities of DSF on a mouse model of spontaneous lung metastasis inoculated with RM72 cells.
Figure 14:
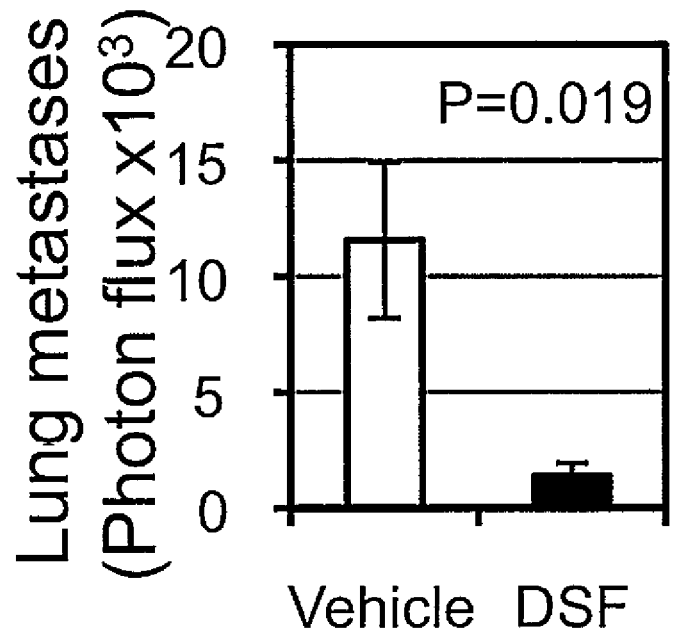
FIG. 14 is a chart of the comparison of the lung metastasis in a vehicle group and a DSF group, showing the anti-tumorigenic and anti-metastatic activities of DSF on a mouse model of spontaneous lung metastasis inoculated with RM72 cells.
Figure 15:
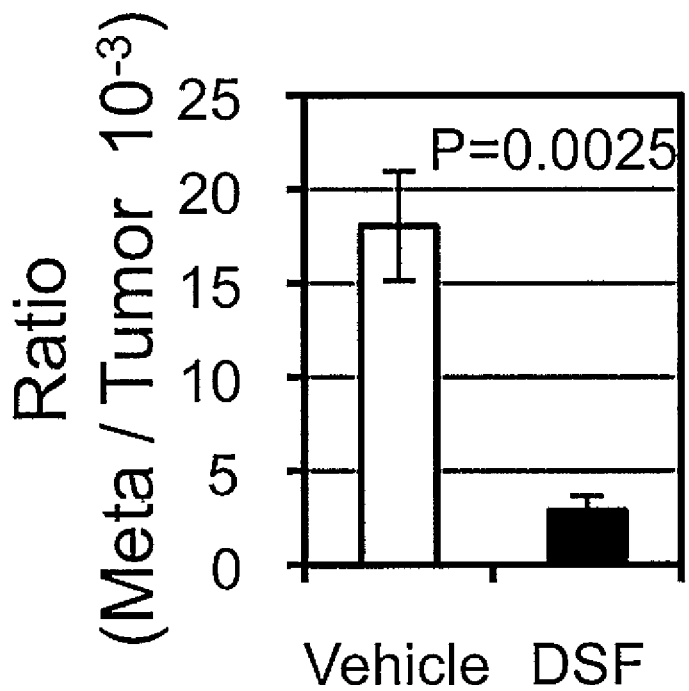
FIG. 15 is a chart of the comparison of the degree of the lung metastasis normalized against the tumor size in a vehicle group and a DSF group, showing the anti-tumorigenic and anti-metastatic activities of DSF on a mouse model of spontaneous lung metastasis inoculated with RM72 cells.

The bioluminescence images of the whole bodies and lungs are shown in FIG. 11. The scattering of the lung metastasis and the tumor size of the individuals are shown in FIG. 12. The comparison of the tumor size in the vehicle group and the DSF group is shown in FIG. 13. The comparison of the lung metastasis in the vehicle group and the DSF group is shown in FIG. 14. The comparison of the degree of lung metastasis normalized against the tumor size is shown in FIG. 15. No serious side effects were observed in any of the subjects in the DSF group. These results revealed that DSF has a weak anti-tumorigenic activity and a strong anti-metastatic activity.

Example 10

Evaluation of Anti-Tumorigenic and Anti-Metastatic Activities of Pyt, Hr, Gra, and Lyc The anti-tumorigenic and anti-metastatic activities of Pyt, Hr, Gra and Lyc were investigated with the same protocol as in Example 9. The experiment was conducted in two batches: Experiment 1 for three groups of a Pyt group, a Hr group and a vehicle group and Experiment 2 for three groups of a Gra group, a Lyc group and a vehicle group. The doses of the test compounds were set at two different quantities considered to be appropriate based on literature (see Tables 3 and 4).

Figure 16:
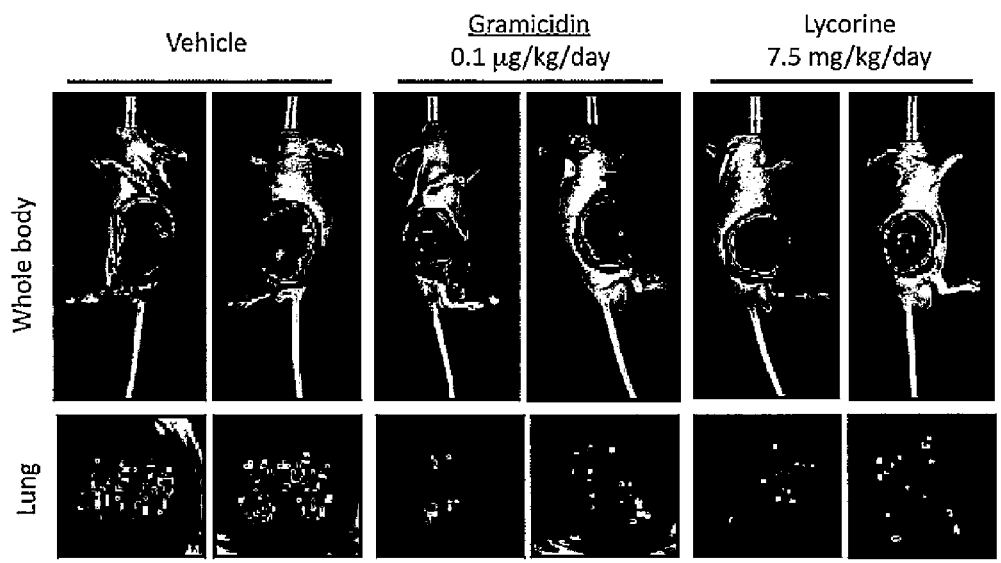
FIG. 16 is bioluminescence images of the whole bodies and lungs of a vehicle group, a Gra group and a Lyc group, showing the anti-tumorigenic and anti-metastatic activities of Gra and Lyc on a mouse model of spontaneous lung metastasis inoculated with RM72 cells.
Figure 17A:
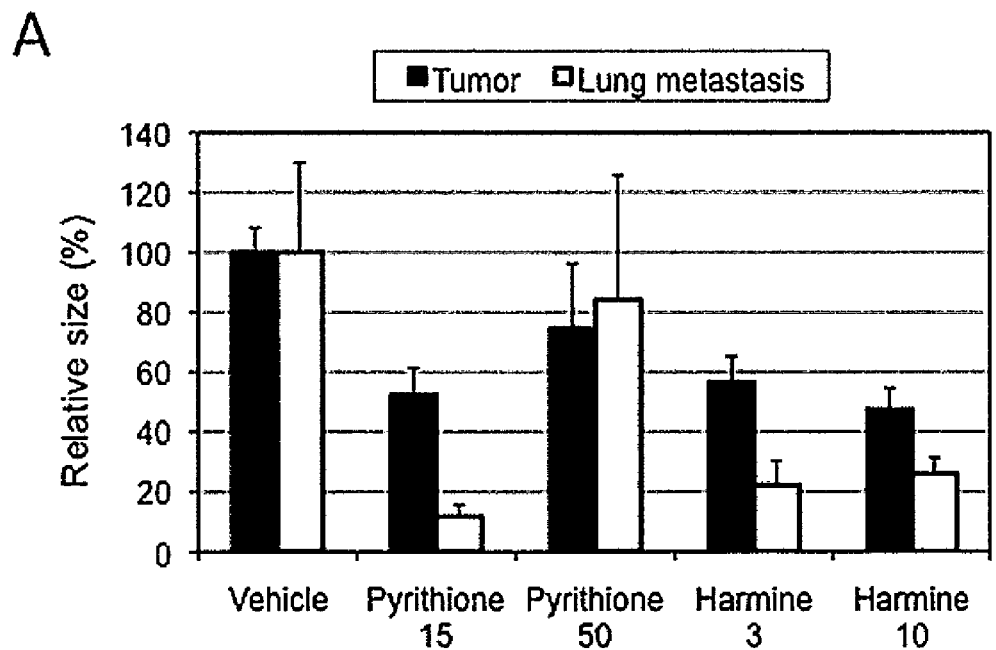
FIG. 17 (A) is a chart of the relative tumor size and relative lung metastasis of Pyt and Hr groups compared to those in a vehicle group, showing the anti-tumorigenic and anti-metastatic activities of Pyt and Hr on a mouse model of spontaneous lung metastasis inoculated with RM72 cells.
Figure 17B:
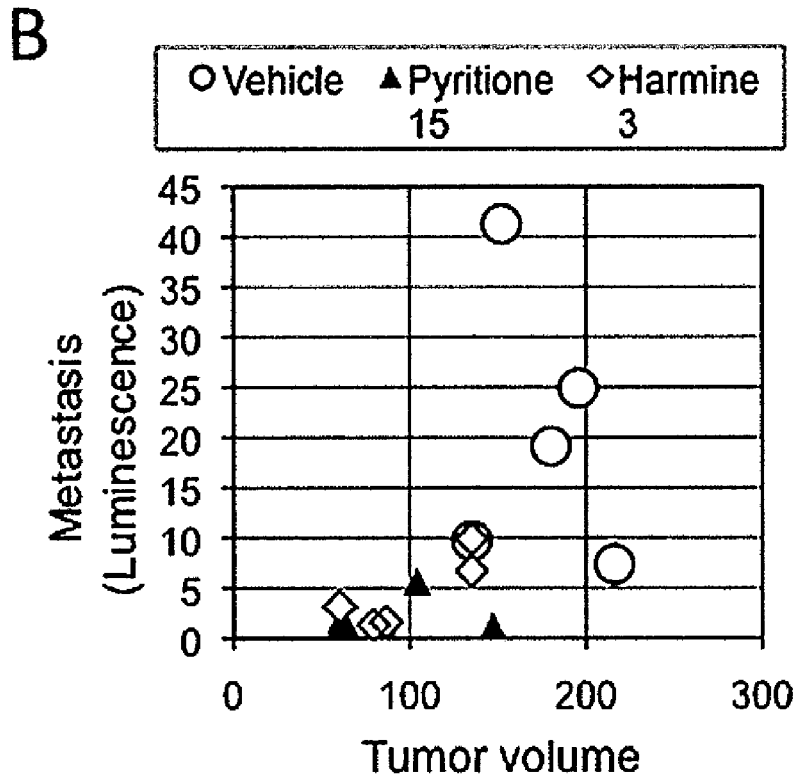
Figure 17C:
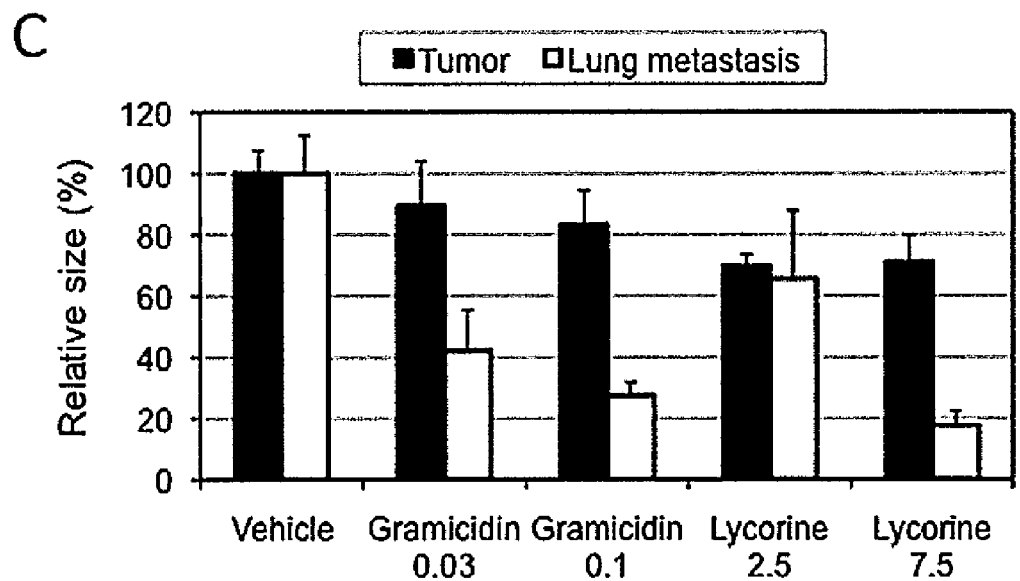
Figure 17D:
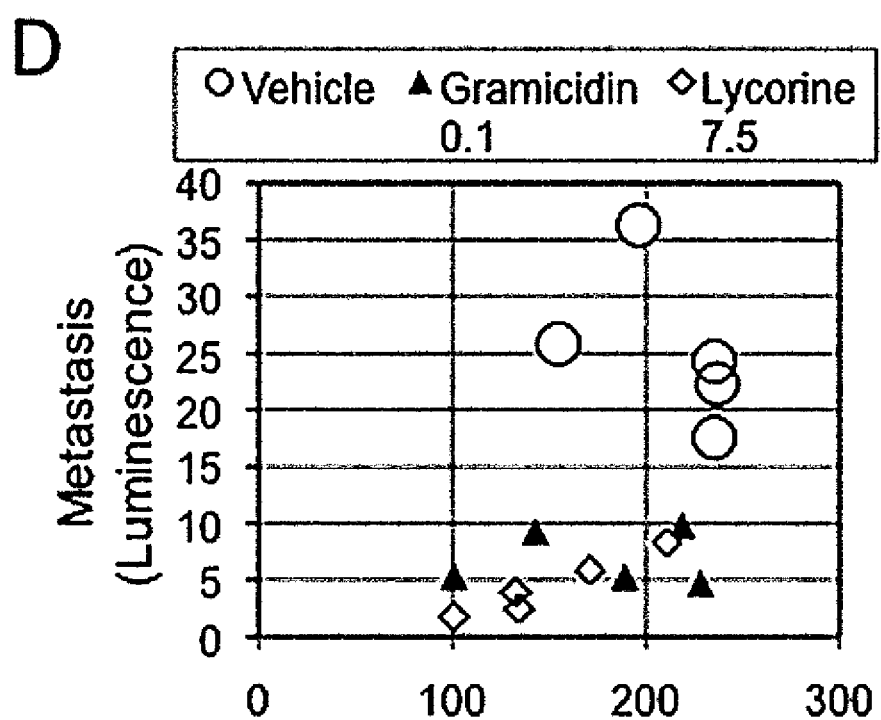

The bioluminescence images of the whole bodies and lungs of the typical individuals in the vehicle, Gra and Lyc groups are shown in FIG. 16. The relative tumor size and relative lung metastasis of the Pyt and Hr groups compared to those in the vehicle group are shown in FIG. 17 (A), the scattering of the lung metastasis and tumor size of the individuals in the Pyt, Hr and vehicle groups are shown in FIG. 17 (B), the relative tumor size and relative lung metastasis of the Gra and Lyc groups compared to those in the vehicle group are shown in FIG. 17 (C), and the scattering of the lung metastasis and tumor size of the individuals in the Gra, Lyc and vehicle groups are shown in FIG. 17 (D). The results of Experiment 1 (the Pyt, Hr and vehicle groups) and Experiment 2 (the Gra, Lyc group, vehicle groups) are summarized in Tables 3 and 4, respectively.

From these results the following findings were obtained and no serious side effects were observed in any of the groups.
(i) Pyt has a strong anti-tumorigenic activity and a strong anti-metastatic activity in a low dose and has a weak anti-tumorigenic activity and a strong anti-metastatic activity in a high dose.
(ii) Hr has a strong anti-tumorigenic and anti-metastatic activities in both doses.
(iii) Gra has a weak anti-tumorigenic activity and a strong anti-metastatic activity in both doses.
(iv) Lyc has a strong anti-tumorigenic activity in both dose and has a strong anti-metastatic activity in a high dose and a weak anti-metastatic activity in a low dose.

TABLE 3

Experiment 1

| Drug and dose | Tumor | | | Lung metastasis | | |
|---|---|---|---|---|---|---|
| (mg/kg/day) | Mean | SEM | p | Mean | SEM | p |
| Vehicle | 100 | 8.3 | | 100 | 29.8 | |
| Pyrithione 15 | 52.2 | 9.08 | 0.0024 | 11.6 | 3.97 | 0.020 |
| Pyrithione 50 | 74.4 | 21.9 | 0.19 | 84.2 | 41.7 | 0.38 |
| Harmine 3 | 56.4 | 8.69 | 0.0034 | 22.0 | 8.03 | 0.029 |
| Harmine 10 | 47.2 | 7.30 | 0.00073 | 25.7 | 5.49 | 0.033 |

TABLE 4

Experiment 2

| Drug and dose | Tumor | | | Lung metastasis | | |
|---|---|---|---|---|---|---|
| (mg/kg/day) | Mean | SEM | p | Mean | SEM | p |
| Vehicle | 100 | 7.64 | | 100 | 12.3 | |
| Gramicidin 0.03 | 89.3 | 14.5 | 0.27 | 42.0 | 13.4 | 0.0065 |
| Gramicidin 0.1 | 83.1 | 11.3 | 0.13 | 27.4 | 4.34 | 0.0013 |
| Lycorine 2.5 | 69.7 | 3.64 | 0.0063 | 65.5 | 22.3 | 0.11 |
| Lycorine 7.5 | 70.9 | 8.89 | 0.019 | 17.7 | 4.71 | 0.00068 |

The above research results confirmed that the spontaneous lung metastasis model using RM72 cells ensures the obtainment of the results in a short period of time with the use of only a small number of animals. This spontaneous lung metastasis model is excellent also in that evaluation of metastasis using the model requires no dissection. The obtainment of the results in a short period of time is crucially important in clinical trials which require daily administration and this experimental system is considered to be useful for making a new breakthrough in preclinical studies.

The compound screening method using a Reck promoter has a feature of both bioactivity-oriented approach employing normal reversion-induction as an indicator and molecular-targeting approach for searching for an activator of the tumor suppressor molecule, RECK. It was revealed that the compound screening method using a Reck promoter can very efficiently find, at the same time, conventional types of anti-cancer drugs and new types of compounds having less toxicity and an anti-metastatic activity, such compounds being represented by DSF.

The present invention is not limited to each embodiment and Example described above, various modifications are possible in the scope of the claims, and any embodiment obtained by combining as appropriate the technical means disclosed in the different embodiments is also within the technical scope of the present invention. All the scientific literature and patent literature described in this application are incorporated herein by reference in their entirety.

Accession No.

Display of a Microorganism
  Identification reference: RM72
  Accession No.: NITE BP-1110
Accession Date
  Jun. 22, 2011
International Trust Authorities
  Name: International Patent Organism Depositary, Incorporated Administrative Agency National Institute of Technology and Evaluation
  Address: 2-5-8 Kazusakamatari, Kisarazu-shi, Chiba, 292-0818 Japan

The invention claimed is:

1. An RM72 cell deposited under the Accession No. NITE BP-1110.

2. An animal model of spontaneous cancer metastasis bearing a tumor formed after inoculation of the cell of claim 1 into the animal.

3. The animal model of spontaneous cancer metastasis of claim 2, wherein the animal is a rodent.

4. The animal model of spontaneous cancer metastasis of claim 3, wherein the animal is a mouse.

5. A method for producing an animal model of spontaneous cancer metastasis, the method comprising inoculating the cell of claim 1 into an experimental animal.

6. The method for producing the animal model of spontaneous cancer metastasis of claim 5, wherein the method comprises subcutaneously inoculating the cell into the experimental animal to develop a tumor.

7. A screening method for a substance having an anticancer activity and/or a cancer metastasis suppressing activity, the method comprising the steps of
  administering a test substance to the animal model of spontaneous cancer metastasis of claim 2, wherein the animal has a tumor,
  determining the tumor size in a cell-inoculation site and/or a metastatic focus number and/or a metastatic focus size in a target organ after the start of the administration of the test substance, and
  comparing the tumor size in the cell-inoculation site and/or the metastatic focus number and/or the metastatic focus size in the target organ between the animal with the administration of the test substance and an animal without the administration of the test substance.

8. A screening method for a substance having an anticancer activity and/or a cancer metastasis suppressing activity, the method comprising the steps of
  administering a test substance to the animal model of spontaneous cancer metastasis of claim 2, administering luciferin to the animal after the start of the administration of the test substance, recording a chemiluminescence image of a cell-inoculation site and/or a target organ of the animal after the administration of luciferin, and comparing the chemiluminescence image of the cell-inoculation site and/or the target organ between the animal with the administration of the test substance and an animal without the administration of the test substance.

9. The screening method of claim 7, wherein the test substance comprises a substance that increases expression of RECK.

* * * * *